US012678198B2

(12) United States Patent
Ali et al.

(10) Patent No.: US 12,678,198 B2
(45) Date of Patent: Jul. 14, 2026

(54) MECHANISMS FOR STRUT LENGTH MEASUREMENT

(71) Applicant: Stryker European Operations Limited, Carrigtwohill (IE)

(72) Inventors: Rustam Ali, Bokaro Steel City (IN); Arpit Gautam, Gurgaon (IN); Manpreet Basur, Faridabad (IN); Somesh Modi, Bikaner (IN); Rajan Yadav, New Delhi (IN); Peter Sterrantino, Palisades Park, NJ (US)

(73) Assignee: Stryker European Operations Limited, Carrigtwohill (IE)

(*) Notice: Subject to any disclaimer, the term of this patent is extended or adjusted under 35 U.S.C. 154(b) by 4 days.

(21) Appl. No.: 19/033,784

(22) Filed: Jan. 22, 2025

(65) Prior Publication Data

US 2025/0255648 A1      Aug. 14, 2025

Related U.S. Application Data

(60) Provisional application No. 63/551,438, filed on Feb. 8, 2024.

(51) Int. Cl.
*A61B 17/64*      (2006.01)
*A61B 17/66*      (2006.01)
*A61B 90/00*      (2016.01)

(52) U.S. Cl.
CPC .......... *A61B 17/6475* (2013.01); *A61B 17/66* (2013.01); *A61B 90/06* (2016.02); *A61B 2090/061* (2016.02)

(58) Field of Classification Search
CPC ..... A61B 17/62; A61B 17/6475; A61B 17/66; A61B 90/06; A61B 2090/061
See application file for complete search history.

(56) References Cited

U.S. PATENT DOCUMENTS

| | | | |
|---|---|---|---|
| 4,973,331 | A | 11/1990 | Pursley |
| 8,834,467 | B2 | 9/2014 | Singh |
| 9,101,398 | B2 | 8/2015 | Singh |
| 10,010,350 | B2 | 7/2018 | Mannanal |
| 10,154,884 | B2 | 12/2018 | Kumar |

(Continued)

FOREIGN PATENT DOCUMENTS

| | | | | | |
|---|---|---|---|---|---|
| CN | 106264693 | A | * | 1/2017 | ............. A61B 17/66 |
| CN | 114505108 | A | * | 5/2022 | ............. B01L 3/021 |

(Continued)

*Primary Examiner* — Jacqueline T Johanas

(74) *Attorney, Agent, or Firm* — SLEMAN & LUND LLP

(57) ABSTRACT

A strut for use with an external fixation system may include first and second joints proximate the first and second ends of the strut, the first and second joints configured to couple to first and second rings of the external fixation system. The strut may include a threaded rod coupled to the first joint, a tube that receives the threaded rod, a fluctuation counter coupled to the tube, and a needle coupled to the fluctuation counter. The needle may extend through a bore in the outer tube, and the needle may have a free end in contact with the threaded rod. The strut may be an adjustable-length strut whereby the threaded rod is moveable axially into or out of the tube, and while the threaded rod moves into or out of the tube, the free end of the needle may be configured to maintain contact with the threaded rod.

10 Claims, 20 Drawing Sheets

(56)                    References Cited

U.S. PATENT DOCUMENTS

| | | | |
|---|---|---|---|
| 10,194,944 B2 | 2/2019 | Edelhauser | |
| 12,465,405 B1 * | 11/2025 | Riccione | ................ A61B 17/62 |
| 2004/0030395 A1 * | 2/2004 | Blunn | ................ A61B 17/7016 |
| | | | 623/23.45 |
| 2011/0004199 A1 | 1/2011 | Ross | |
| 2016/0030085 A1 | 2/2016 | Ross | |
| 2023/0193936 A1 | 6/2023 | Pak | |
| 2023/0255665 A1 | 8/2023 | Pak | |
| 2025/0255648 A1 * | 8/2025 | Ali | ..................... A61B 17/6475 |

FOREIGN PATENT DOCUMENTS

| | | | | | |
|---|---|---|---|---|---|
| CN | 120379606 A | * | 7/2025 | ............. | B25B 21/00 |
| EP | 4491332 A2 | * | 1/2025 | ............. | B25B 21/00 |
| EP | 4599778 A1 | * | 8/2025 | ............. | A61B 17/66 |
| RU | 2744655 C1 | * | 3/2021 | ............. | A61B 17/60 |

* cited by examiner

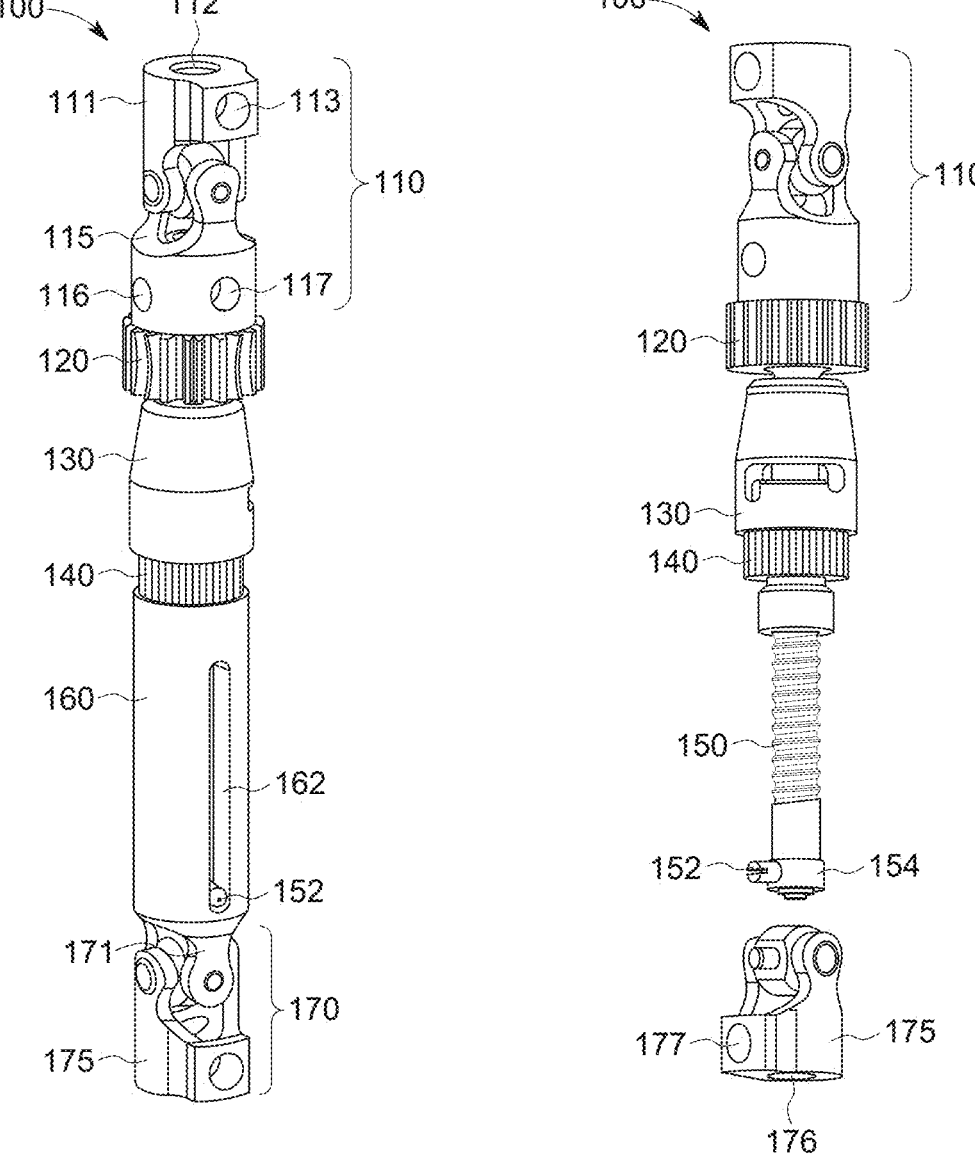
FIG. 2A                    FIG. 2B

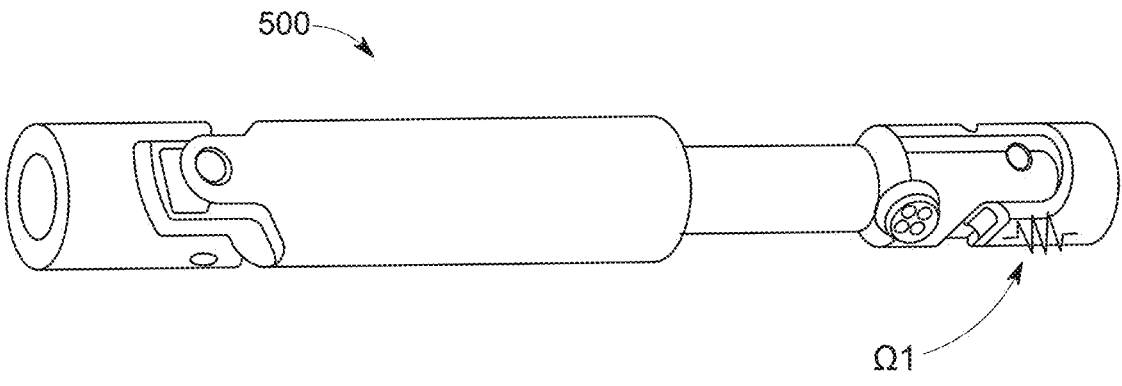
FIG. 6F
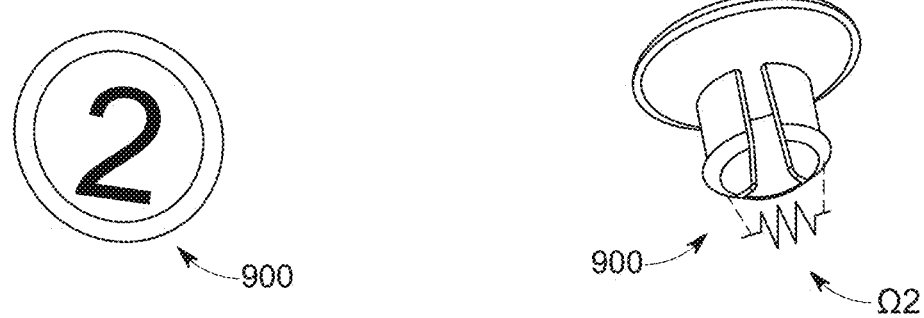
FIG. 6G                    FIG. 6H

| Strut Type | Strut Position | | | | | |
| | Position 1 (10 Ohms) | Position 2 (20 Ohms) | Position 3 (30 Ohms) | Position 4 (40 Ohms) | Position 5 (50 Ohms) | Position 6 (60 Ohms) |
|---|---|---|---|---|---|---|
| Mini Strut (2 Ohms) | 12 Ohms | 22 Ohms | 32 Ohms | 42 Ohms | 52 Ohms | 62 Ohms |
| Extra Short Strut (4 Ohms) | 14 Ohms | 24 Ohms | 34 Ohms | 44 Ohms | 54 Ohms | 64 Ohms |
| Short Strut (6 Ohms) | 16 Ohms | 26 Ohms | 36 Ohms | 46 Ohms | 56 Ohms | 66 Ohms |
| Medium Strut (8 Ohms) | 18 Ohms | 28 Ohms | 38 Ohms | 48 Ohms | 58 Ohms | 68 Ohms |
| Long Strut (10 Ohms) | 20 Ohms | 30 Ohms | 40 Ohms | 50 Ohms | 60 Ohms | 70 Ohms |

FIG. 6J

MECHANISMS FOR STRUT LENGTH MEASUREMENT

CROSS-REFERENCE TO RELATED APPLICATIONS

This application claims priority to the filing date of U.S. Provisional Patent Application No. 63/551,438, filed Feb. 8, 2024, the disclosure of which is hereby incorporated by reference herein.

BACKGROUND OF THE DISCLOSURE

The present disclosure relates to systems and components of external fixation frames. More particularly, the present disclosure relates to struts and strut components using gear mechanisms and/or controller modules for manipulation of an external fixation frame.

Many different types of bone deformities can be corrected using external fixation systems to perform the distraction osteogenesis process. For example, an Ilizarov device or similar external fixation system may be used. Such systems generally use rings also designated as fixation plates connected by threaded rods or struts for manipulation, lengthening, angulation, rotation, and/or translation of deformities of bones.

As the struts are manipulated, the rings or fixation plates change positions relative to one another, causing the bones or bone segments attached to the fixation plates to change positions relative to one another, until the bone segments are in a desired position relative to one another. Fixation systems have many areas which may be improved including, for example, the ease and precision with which lengths of the struts may be measured during a correction procedure.

BRIEF SUMMARY

According to one aspect of the disclosure, a strut for use with an external fixation system may include a first joint proximate a first end of the strut, the first joint configured to couple to a first ring of the external fixation system. The strut may include a second joint proximate a second end of the strut, the second joint configured to couple to a second ring of the external fixation system. The strut may include a threaded rod having a first end coupled to the first joint, a tube that receives the threaded rod, a fluctuation counter coupled to the tube, and a needle coupled to the fluctuation counter. The needle may extend through a bore in the outer tube and may have a free end in contact with the threaded rod. The strut may be an adjustable-length strut whereby the threaded rod is moveable axially into or out of the tube, and while the threaded rod moves into or out of the tube, the free end of the needle is configured to maintain contact with the threaded rod. While the threaded rod moves into or out of the tube, the free end of the needle may be configured to maintain contact with the threaded rod by riding along peaks and valleys of threads of the threaded rod. As the free end of the needle rides along peaks and valley of threads of the threaded rod, a position of the fluctuation counter may be configured to fluctuate relative to the outer tube. The fluctuation counter may be configured to count a total number of fluctuations as the free end of the needle rides along peaks and valleys of threads of the threaded rod, with one fluctuation corresponding to one complete revolution of the threaded rod.

According to another aspect of the disclosure, a method of determining a change in length of a strut of an external fixation system may include axially translating a threaded rod of the strut into or out of a tube of the strut to increase or decrease an effective length of the strut such that, during the axial translating, a free end of a needle that is coupled to a fluctuation counter that is coupled to the tube moves radially inward toward thread valleys of the threaded rod or radially outward toward threads peaks of the threaded rod. The method may include counting, via the fluctuation counter, a total number of fluctuation cycles of the needle, each fluctuation cycle corresponding to one revolution of the threaded rod relative to the tube. The method may also include determining a total length change of the strut by multiplying the total number of fluctuation cycles by a pitch of the threaded rod. Each time the free end of the needle moves from one peak of the threaded rod to an axially adjacent peak of the threaded rod, the fluctuation counter may increase the total number of counted fluctuation cycles by one. Each time the free end of the needle moves from one valley of the threaded rod to an axially adjacent valley of the threaded rod, the fluctuation counter may increase the total number of counted fluctuation cycles by one. Prior to counting the total number of fluctuation cycles of the needle, the total number of counted fluctuation cycles may be set to zero. Prior to determining the length change of the strut, the pitch of the threaded rod may be entered into software of a computer system. After counting the total number of fluctuation cycles of the needle, the total number of counted fluctuation cycles may be entered into the software of the computer system, and the step of determining the total length change of the strut may be performed using the software of the computer system.

According to a further aspect of the disclosure, a strut for use with an external fixation system may include a first joint proximate a first end of the strut, the first joint configured to couple to a first ring of the external fixation system. The strut may include a second joint proximate a second end of the strut, the second joint configured to couple to a second ring of the external fixation system. The strut may include a threaded rod having a first end coupled to the first joint, a tube that receives the threaded rod, and a pointer secured to a second end of the threaded rod. The pointer may extend through an axially-extending slot of the tube and the pointer may have a collar and a fastener extending through the collar to secure the pointer to the threaded rod. A sensor may be coupled to the collar. The strut may include a plurality of rows of pits formed in an inner surface of the tube, each row of pits having a unique shape combination corresponding to a unique length value. The threaded rod may be configured to move into or out of the tube to change an effective length of the strut, and the pointer may be rotationally fixed to the tube so that, as the effective length of the strut changes, the sensor maintains a rotational position relative the inner surface of the tube in which the sensor points toward at least one of the plurality of rows of pits. There may be a total number of ten uniquely shapes pits, and each uniquely shaped pit may correspond to a numeral between 0 and 9. The plurality of rows of pits may be organized into three columns, a first of the three columns corresponding to a single-digit place, a second of the three columns corresponding to a double-digit place, and a third of the three columns corresponding to a triple-digit place. The sensor may be an array or matrix of ultrasonic sensors. The sensor may be an array or matrix of optical sensors. The sensor may be a camera.

According to yet a further aspect of the disclosure, a method of determining a length of a strut of an external fixation system may include axially translating a threaded rod of the strut into or out of a tube of the strut to increase or decrease an effective length of the strut, the strut including a pointer secured to an end the threaded rod, the pointer extending through an axially-extending slot of the tube, the pointer having a collar, a fastener extending through the collar to secure the pointer to the threaded rod. During the axial translating, a sensor on the collar may axially translate relative to the tube but remain rotationally fixed relative to the tube. The sensor may capture one row of pits of a plurality of rows of pits formed in an inner surface of the tube. Based on the captured row of pits, a length of the strut may be determined based on correspondence between a unique shape combination of the row of pits and a unique length value. There may be a total number of ten uniquely shapes pits, each uniquely shaped pit corresponding to a numeral between 0 and 9. The plurality of rows of pits may be organized into three columns, a first of the three columns corresponding to a single-digit place, a second of the three columns corresponding to a double-digit place, and a third of the three columns corresponding to a triple-digit place. The sensor may be an array or matrix of ultrasonic sensors. The sensor may be an array or matrix of optical sensors. The sensor may be a camera.

According to still another aspect of the disclosure, a strut system for use with an external fixation system may include a first joint proximate a first end of the strut, the first joint configured to couple to a first ring of the external fixation system. The strut system may include a second joint proximate a second end of the strut, the second joint configured to couple to a second ring of the external fixation system. The strut system may include a threaded rod having a first end coupled to the first joint, a tube that receives the threaded rod, and a pointer secured to a second end of the threaded rod. The pointer may extend through an axially-extending slot of the tube, and the pointer may have a collar and a fastener extending through the collar to secure the pointer to the threaded rod. The threaded rod may be configured to move into or out of the tube to change an effective length of the strut, and the pointer may be rotationally fixed to the tube so that, as the effective length of the strut changes, pointer is configured to move axially along the slot of the tube. The strut system may include a plurality of optical markings on an outer surface of the tube adjacent to the axially-extending slot, and each optical marking may correspond to a unique length value. The strut system may include a camera configured to determine which of the plurality of optical markings aligns with the pointer at a given effective length of the strut, and may be further configured to correlate the optical marking aligned with the pointer into a length value that indicates the effective length of the strut.

According to yet another aspect of the disclosure, a method of determining a length of a strut of an external fixation system may include axially translating a threaded rod of the strut into or out of a tube of the strut to increase or decrease an effective length of the strut, the strut including a pointer secured to an end the threaded rod, the pointer extending through an axially-extending slot of the tube such that the pointer moves axially along the axially-extending slot as the threaded rod translates into or out of the tube. An image may be captured, via a camera, of a position of the pointer relative to a plurality of optical markings on an outer surface of the tube adjacent to the axially-extending slot. The method may include determining which of the plurality of optical markings aligns with the pointer. The method may include displaying, on a display device associated with the camera, a total length of the strut based on a known relationship between (i) the optical marking that aligns with the pointer and (ii) strut length. Each of the plurality of optical markings may correspond to a different strut length.

According to another aspect of the disclosure, a strut for use with an external fixation system may include a first joint proximate a first end of the strut, the first joint configured to couple to a first ring of the external fixation system. The strut may include a second joint proximate a second end of the strut, the second joint configured to couple to a second ring of the external fixation system. The strut may include a threaded rod having a first end coupled to the first joint, an outer tube that receives the threaded rod, an inner tube received between the outer tube and the threaded rod, and a connector on the strut. The strut may include a first electrically conductive wire coupled to the outer tube, a second electrically conductive wire coupled to the inner tube, and a third electrically conductive wire coupled to the threaded rod. An electrically conductive loop may be formed between the connector, the first electrically conductive wire, the second electrically conductive wire, and the third electrically conductive wire, a length of the loop changing as an effective length of the strut changes. The inner tube may be configured to axially translate relative to the outer tube in a rapid adjustment stage, and the electrically conductive loop may be a first electrically conductive loop, and the length of the first loop may change during the rapid adjustment stage. The strut may include a second electrically conductive loop that is formed between the connector, the first electrically conductive wire, and the third electrically conductive wire. The threaded rod may be configured to axially translate relative to the outer tube in a gradual adjustment stage, and a length of the second electrically conductive loop may be configured to change during the gradual adjustment stage. The strut may include an internal resistance value that corresponds to a size of the strut. The strut may include a strut clip configured to clip onto the strut, the strut clip having an internal resistance value that corresponds to a position identifier of the strut clip.

According to still another aspect of the disclosure, a method of determining a length of a strut of an external fixation system may include coupling a connector of a portable device to a connector of the strut and applying electrical current to the connector of the strut. The method may include allowing the electrical current to travel along an electrically conductive loop, the electrically conductive loop defined at least in part by a first electrically conductive wire coupled to an outer tube of the strut, a second electrically conductive wire coupled to an inner tube of the strut positioned within the outer tube, and a third electrically conductive wire coupled to a threaded rod at least partially received within the inner tube. The method may include determining, via the portable device, a resistance of the electrically conductive loop. The method may include, based on the determined resistance, determining an effective length of the strut. The method may include performing a first calibration prior to determining the effective length of the strut. Performing the first calibration may include: (i) when the strut is at a minimum length, coupling the connector of the portable device to the connector of the strut and applying electrical current to the connector of the strut; (ii) allowing the electrical current to travel along the electrically conductive loop while the electrically conductive loop is at a minimum length corresponding to the minimum length of the strut; (iii) determining, via the portable device, the resistance of the electrically conductive loop while the electrically conductive loop is at the minimum length; and (iv) setting, in a calibration device, the resistance of the electrically conductive loop while the electrically conductive loop is at the minimum length to correspond to the minimum length of the strut. The method may include performing a second calibration prior to determining the effective length of the strut. Performing the second calibration may include: (i) when the strut is at a maximum length, coupling the connector of the portable device to the connector of the strut and applying electrical current to the connector of the strut; (ii) allowing the electrical current to travel along the electrically conductive loop while the electrically conductive loop is at a maximum length corresponding to the maximum length of the strut; (iii) determining, via the portable device, the resistance of the electrically conductive loop while the electrically conductive loop is at the maximum length; and (iv) setting, in the calibration device, the resistance of the electrically conductive loop while the electrically conductive loop is at the maximum length to correspond to the maximum length of the strut. The method may also include coupling the connector of a portable device to the connector of the strut and applying electrical current to the connector of the strut, and allowing the electrical current to travel along an electrically conductive pathway that passes through an internal resistor of the strut and an internal resistor of a strut clip that is coupled to the strut. The internal resistor of the strut may have a known resistance value that corresponds to a type of strut, and the internal resistor of the strut clip may have a known resistance value that corresponds to a position of the strut. The method may also include determining a total resistance along the electrically conductive pathway that passes through the internal resistor of the strut and the internal resistor of a strut clip, and based on the determined total resistance, determining the type of the strut and the position of the strut.

BRIEF DESCRIPTION OF THE DRAWINGS

FIG. 2A is a perspective view of a strut of the external fixation system of FIG. 1.

FIGS. 2B-C are a perspective views of the strut of FIG. 2A with certain components omitted.

FIG. 2D is a perspective view of an actuation mechanism of the strut of FIG. 2A.

6

Figure 6A:
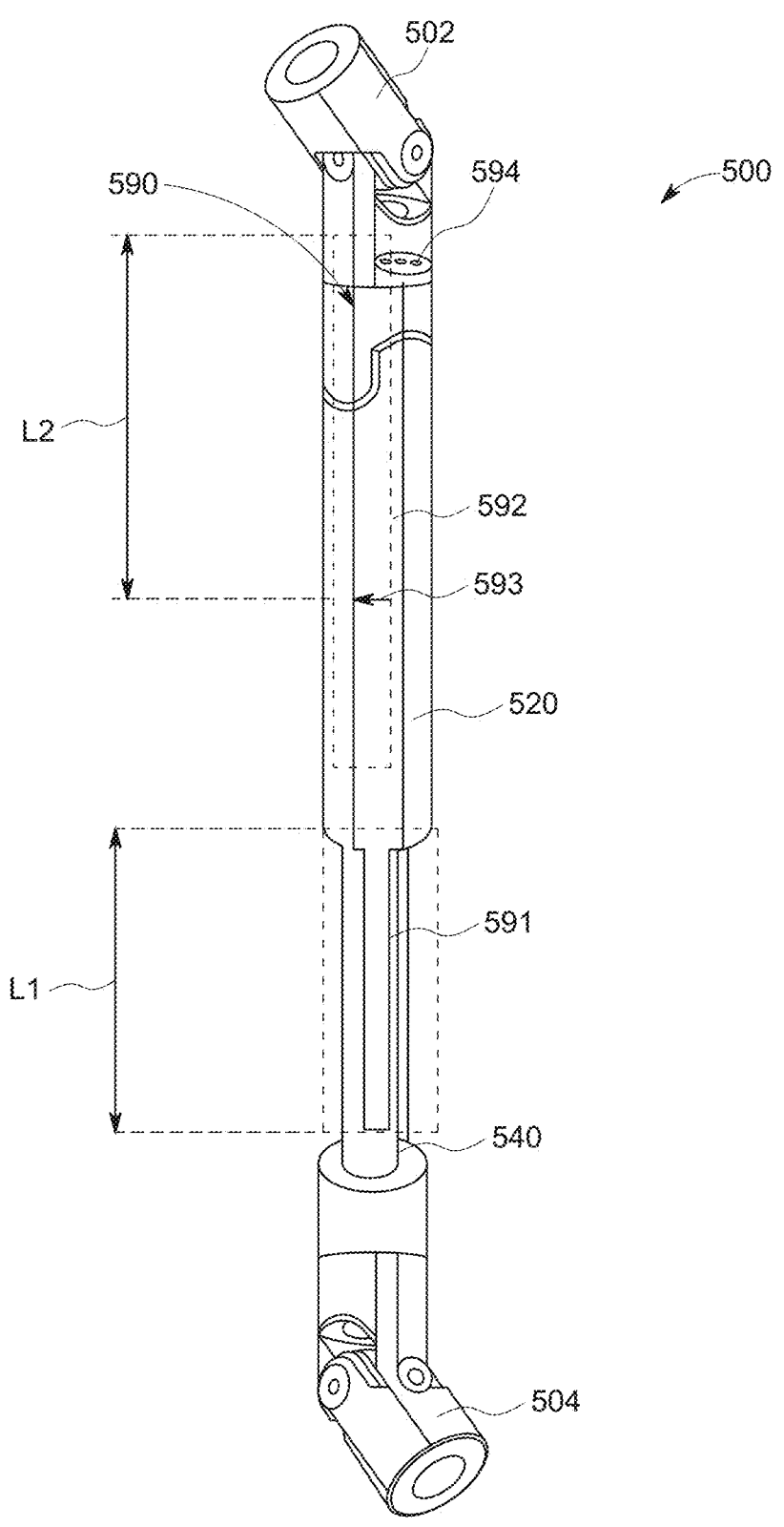

FIG. 6A is front view of an example of a strut, shown in partial phantom, having another embodiment of a length measurement mechanism.

Figure 6B:
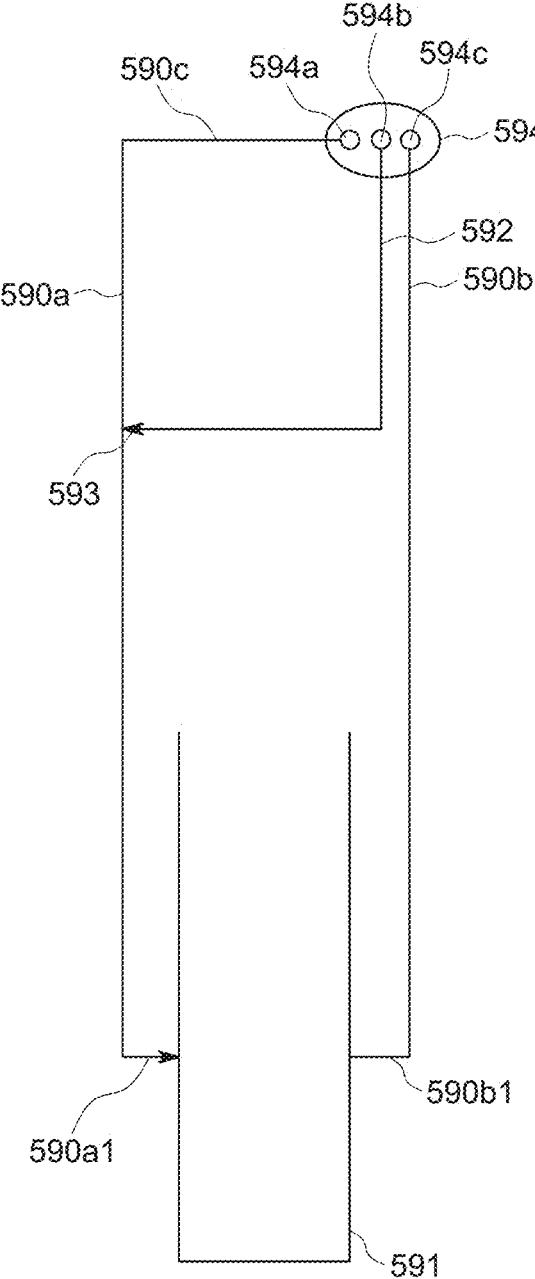

FIG. 6B is a highly schematic circuit diagram of resistance wires of the strut of FIG. 6A.

Figure 6C:
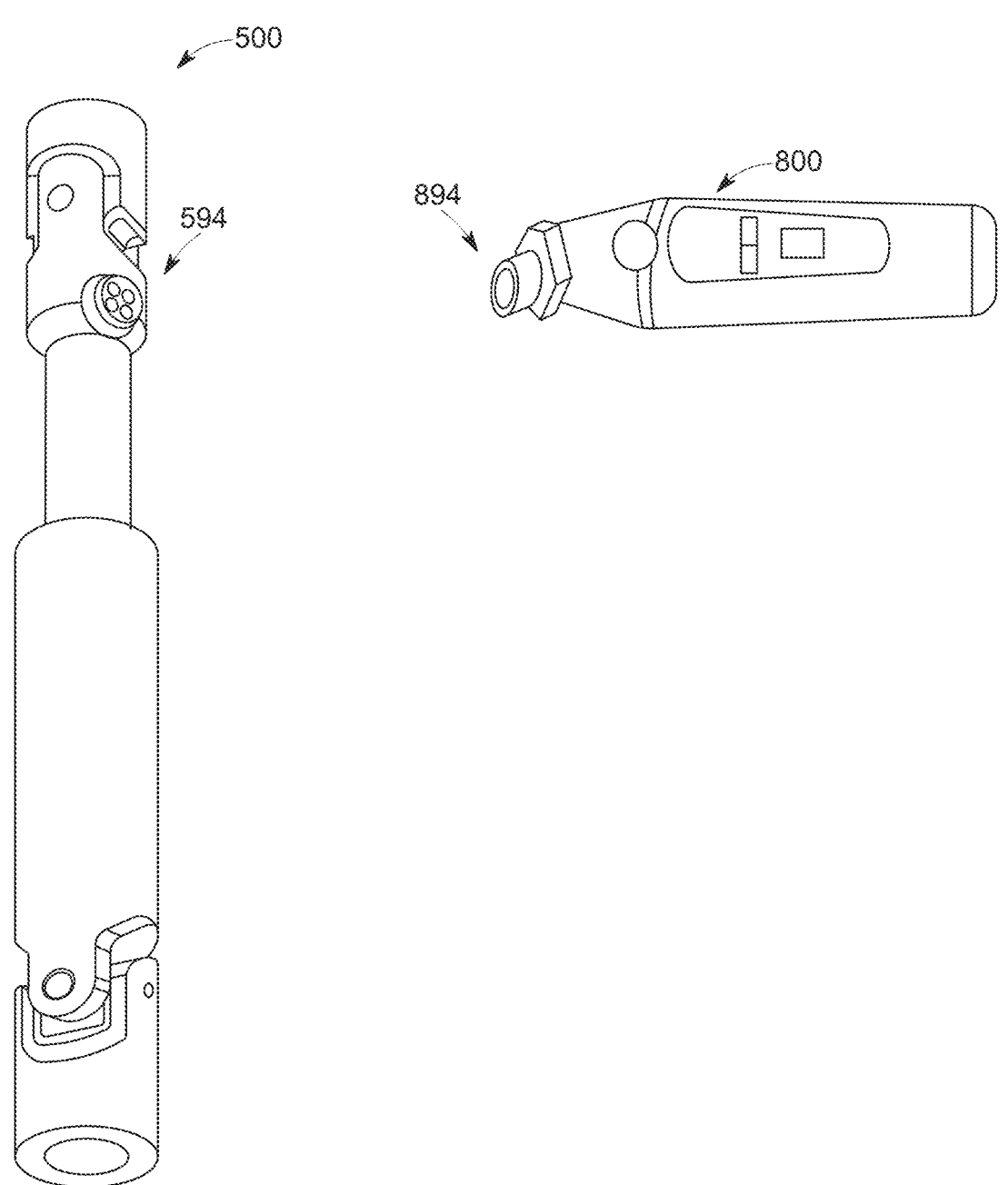

FIG. 6C illustrates a portable device being connected to the strut of FIG. 6A.

Figure 6D:
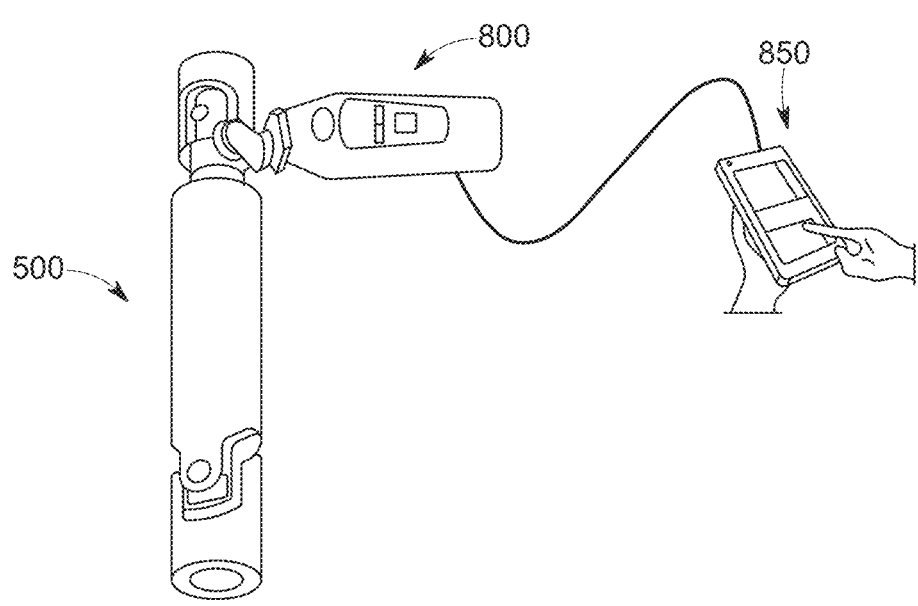
Figure 6E:
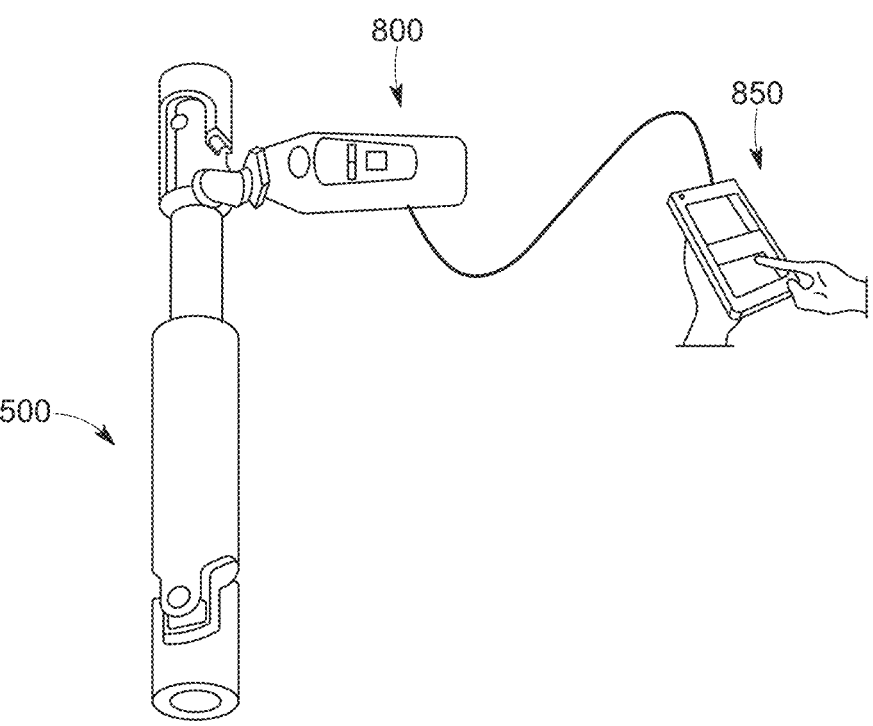

FIGS. 6D-6E illustrate two individual stages of a calibration process using the portable device of FIG. 6C and a calibration device.

FIG. 6F shows an example of a medium-length strut having an internal resistance.

FIGS. 6G-6H show examples of a strut clip for a second position, the strut clip having an internal resistance.

Figure 6I:
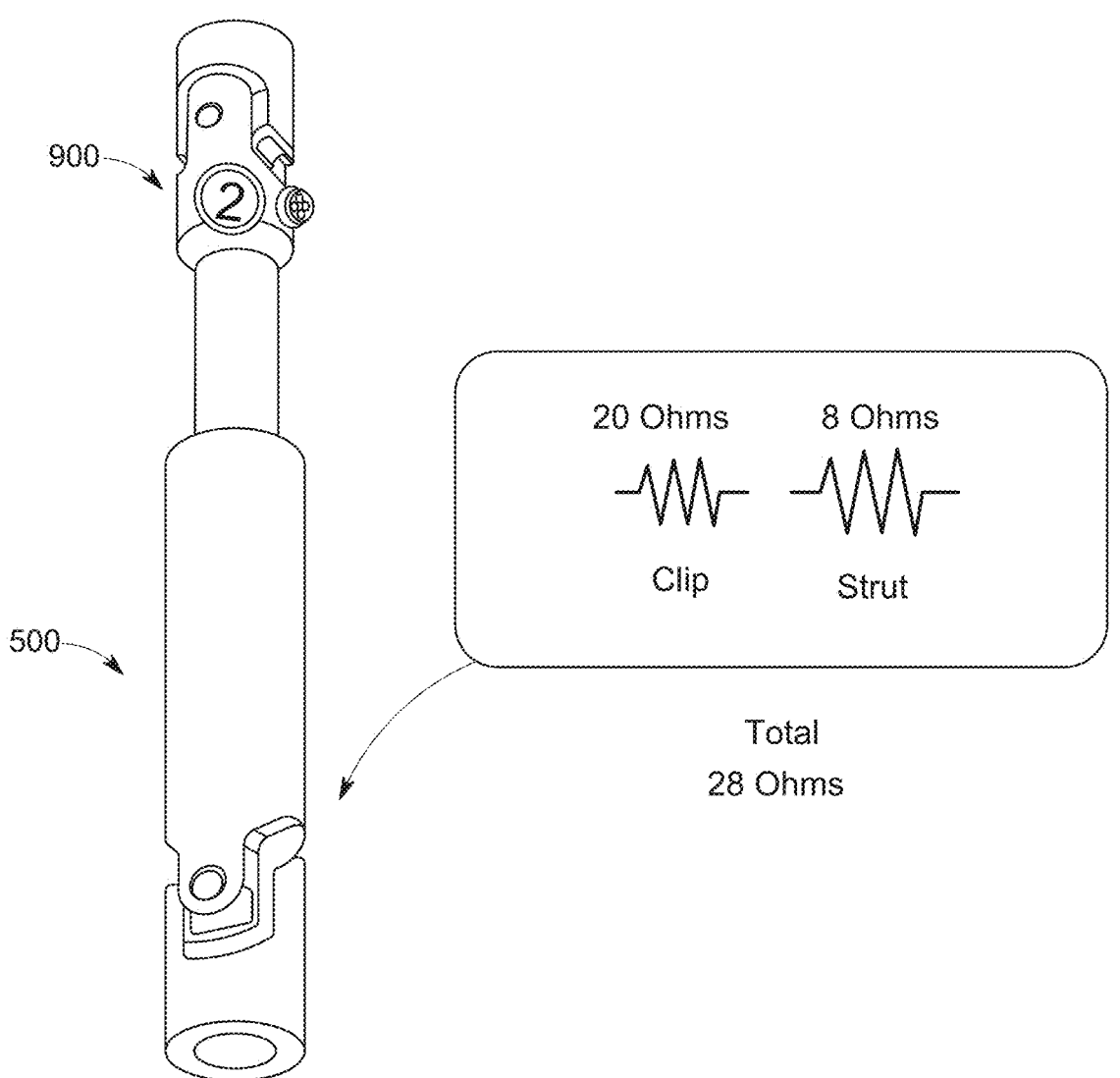

FIG. 6I shows an example of a medium length strut with a second position strut clip providing for a total internal resistance value.

FIG. 6J shows a chart illustrating unique values of combined internal resistances for different types of struts and different position strut clips.

Figure 6K:
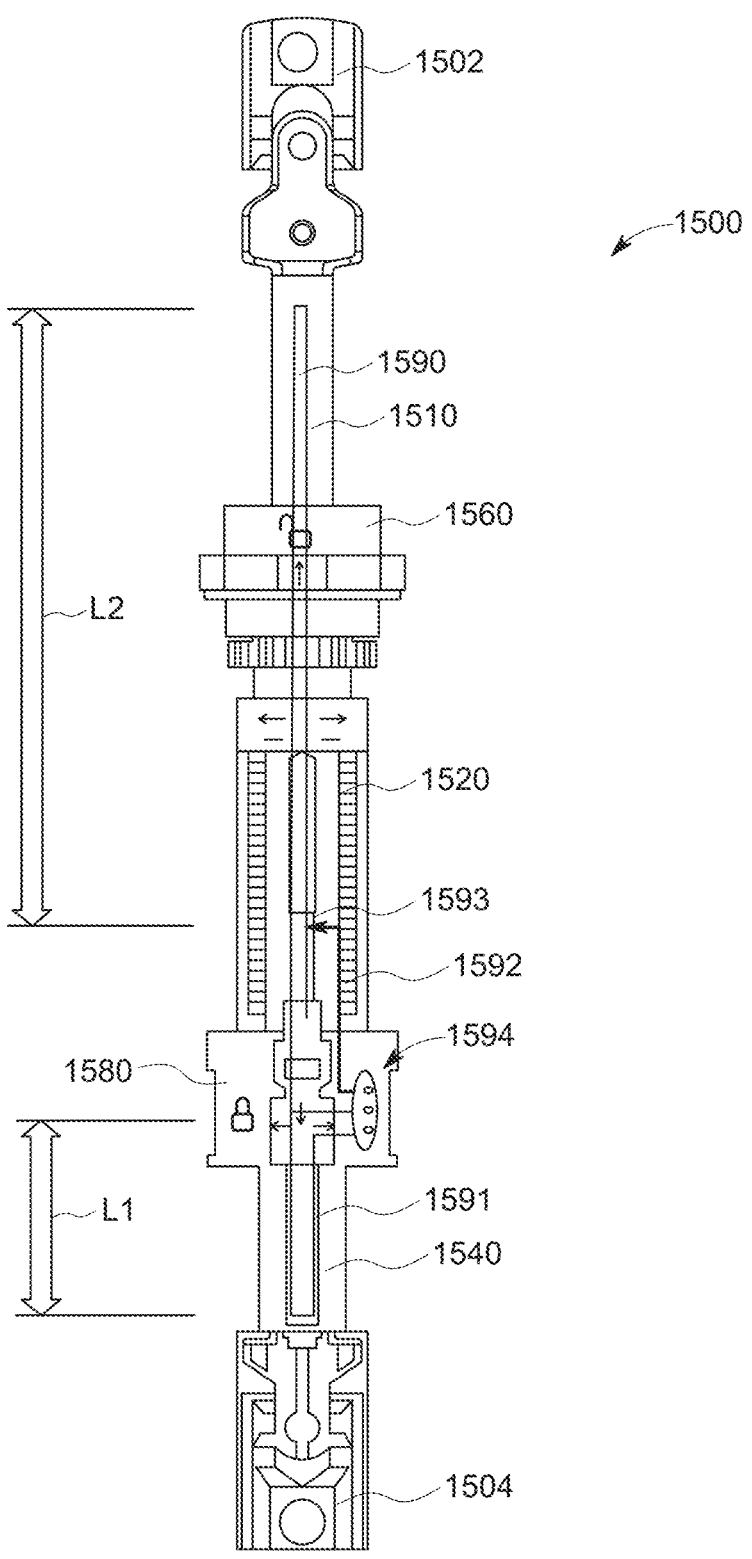

FIG. 6K is front view of an example of a strut, shown in partial phantom, having another embodiment of a length measurement mechanism similar to that shown in FIG. 6A.

Figure 6L:
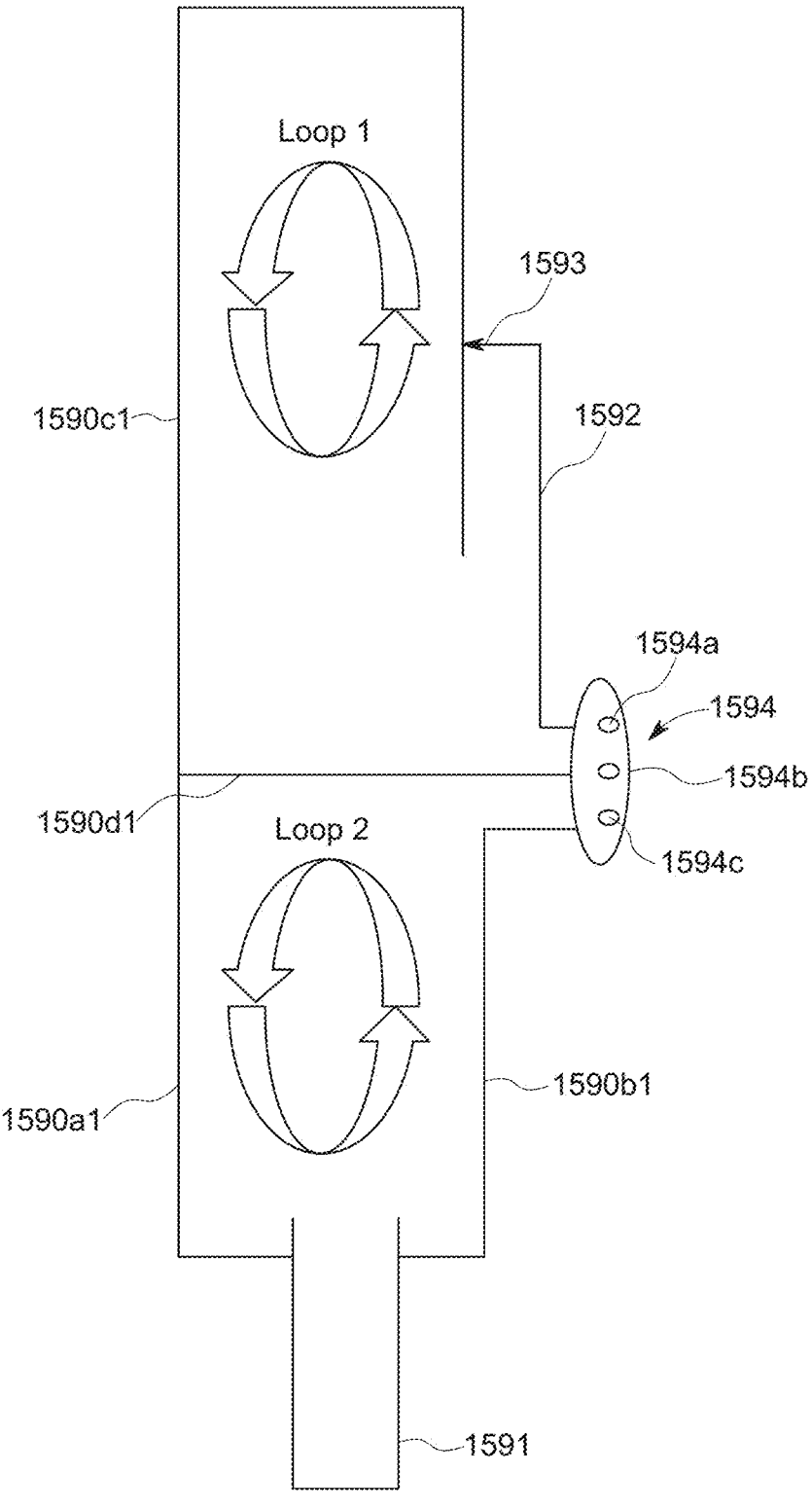

FIG. 6L is a highly schematic circuit diagram of resistance wires of the strut of FIG. 6B.

DETAILED DESCRIPTION

Figure 1:
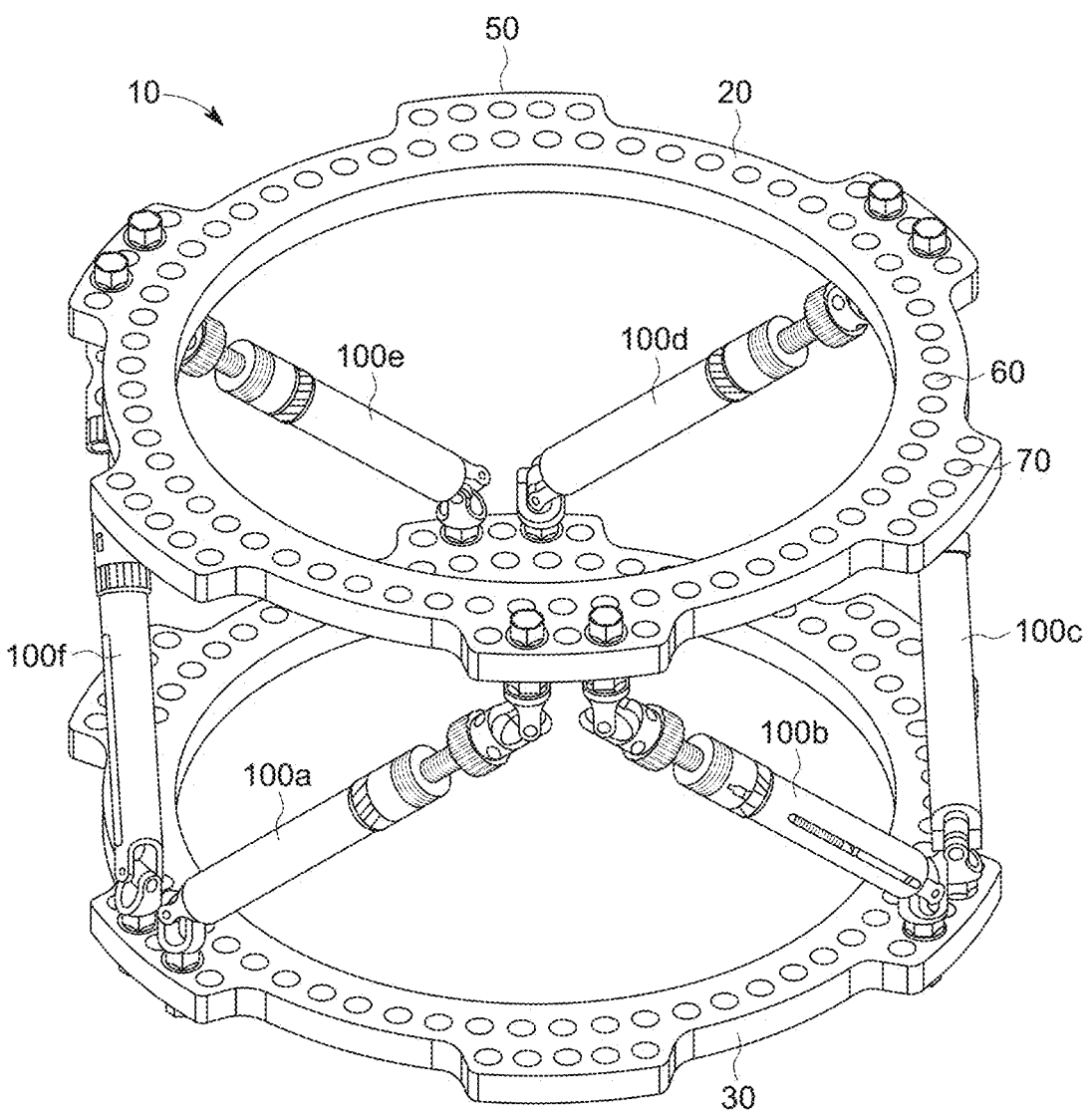
FIG. 1 is a perspective view of an external fixation system according to an embodiment of the disclosure.

FIG. 1 shows an external fixation frame 10 in an assembled condition according to one aspect of the disclosure. Generally, fixation frame 10 includes a first ring 20 and a second ring 30, with six adjustable length telescopic struts 100a-f coupling the first ring 20 to the second ring 30. The first ring 20 may also be referred to as a proximal ring or a reference ring, while the second ring 30 may also be referred to as a distal ring or a moving ring. In the illustrated embodiment, each strut 100a-f includes a threaded portion that may thread into or out of a tube portion, for example by interaction with quick release mechanism 130, to decrease or increase the length, respectively, of the telescopic strut. Each end of each strut 100a-f may be coupled to the first ring 20 and second ring 30 via a joint mechanism, such as a ball joint, a constrained hinge joint, or a universal joint as illustrated. The use of universal joints on each end of the strut provides for six degrees of freedom of motion of the external fixation system 10. It should be understood that although the disclosure is generally described in the context of closed circular rings, the concepts described herein may apply with equal force to other types of rings, such as open rings and/or U-shaped rings.

In external fixation system 10, telescopic struts 100a-f are used to reduce fractures and/or correct deformities over time. Patients correct the deformities by prescribed adjustments of the struts 100a-f. The lengths of the struts 100a-f are adjusted over time to change the position and orientation of the two rings 20, 30 with respect to one another, which in turn repositions and reorients the bone fragments, with a goal of correcting the bone deformity. The adjustment of the external fixator 10 should strictly comply with the predetermined correction plan.

Rings 20 and 30 of external fixation system 10 may include a plurality of extension tabs 50. In the illustrated example, each ring 20 and 30 includes six extension tabs 50 spaced circumferentially around the perimeter of the respective rings, although more or fewer may be suitable depending on the particular components of the fixation system. In addition to what is described directly below, extension tabs 50 may help increase the cross-sectional area of rings 20, 30 and thus provide for increased stiffness of the rings.

With this configuration, each ring 20, 30 includes a first inner circumferential row of holes 60 and a second outer circumferential row of holes 70. As illustrated, the second outer circumferential row of holes 70 may be only positioned on the plurality of extension tabs 50 on the rings 20 and 30. It should be understood that although the second outer circumferential row of holes 70 is shown in FIG. 1 as being positioned solely on extension tabs 50, top ring 20 and/or bottom ring 30 may contain two complete rows of holes, for example with a completely circular (or nearly completely circular) geometry. The use of extension tabs 50, compared to two full circumferential rows of holes, may help reduce overall bulk of rings 20, 30 and also provide for intuitive strut placement for surgical personnel. The completely circular version of rings 20, 30 with two full (or nearly full) rows of circumferential holes may be particularly suited for relatively small diameter rings, although indentations or other features may be introduced to provide an intuitive interface for strut placement by surgical personnel. Further, in the illustrated embodiment, the first and second circumferential rows of holes 60 and 70 are positioned so that the first row of holes 60 does not align radially with the second row of holes 70. In other words, the first row of holes 60 has a staggered configuration with respect to the second row of holes 70. The additional hole options may also be utilized for connecting other components, such as fixation pins to couple the rings 20, 30 to the respective bone fragments. Still further, the staggered configuration of holes between the first and second rows 60, 70 may also help prevent interference between components attached to nearby holes, for example such as a strut 100a-f positioned in a first hole and a fixation pin or other fixation member attached to an adjacent or nearby second hole. For example, a relatively thin wire extending radially from one of the holes in the first circumferential row 60 may not radially interfere with a hole positioned in the second circumferential row 70 because of the radial staggering. It should be understood that the size of the tabs 50 may increase or decrease depending on the diameter of the rings 20 and 30, with greater diameter rings 20 and 30 having larger tabs 50 with more holes 70 compared to smaller diameter rings. For example, the illustrated tabs 50 include six holes 70, and a smaller ring may include smaller tabs with four holes each, for example.

FIG. 2A illustrates a perspective view of one telescopic strut 100 from the external fixation system 10 of FIG. 1. It should be understood that the components of struts 100a-f may be identical to one another, although some struts 100a-f may have different sizes than other struts 100a-f and may include different indicia, such as colors or markings for identification purposes, as described in greater detail below. For purposes of this disclosure, the term proximal refers to the top of the strut 100 in the orientation of FIG. 2A, and the term distal refers to the bottom of the strut 100 in the orientation of FIG. 2A. The proximal end portion of strut 100 may include a first joint 110, which is shown in this example as a universal joint. Joint 110 may include a proximal portion 111, which may include a first aperture 112 aligned substantially parallel with the longitudinal axis of strut 100 and a second aperture 113 aligned substantially transverse or orthogonal to the first aperture 112. The first aperture 112 may be configured to receive a fastener that passes through a hole in proximal ring 20 to secure the proximal portion 111 of joint 110 to proximal ring 20. The fastener may be connected so that the proximal portion 111 does not rotate relative to proximal ring 20. The second aperture 113 may be configured to receive a portion of a tool to prevent proximal portion 111 from rotating, for example while a fastener is being screwed into or otherwise inserted into first aperture 112. Joint 110 may also include a distal portion 115 with a first aperture 116 and a second aperture 117, the first and second apertures 116, 117 being aligned substantially transverse and/or orthogonal to one another and to the longitudinal axis of strut 100. First and second apertures 116, 117 may be used as attachment points for attaching additional components to strut 100.

Still referring to FIG. 2A, strut 100 may include additional components including an actuation mechanism 120, a quick-release mechanism 130, a strut identifier 140, a threaded rod 150 (not visible in FIG. 2A), a tube 160, and a second joint 170. As noted above, the effective length of strut 100, which may be thought of as the distance between the proximal end and distal end of strut 100, may be adjusted by threading the threaded rod 150 of strut 100 into or out of tube 160 through interaction with quick-release mechanism 130.

Figures 2C, 2D:
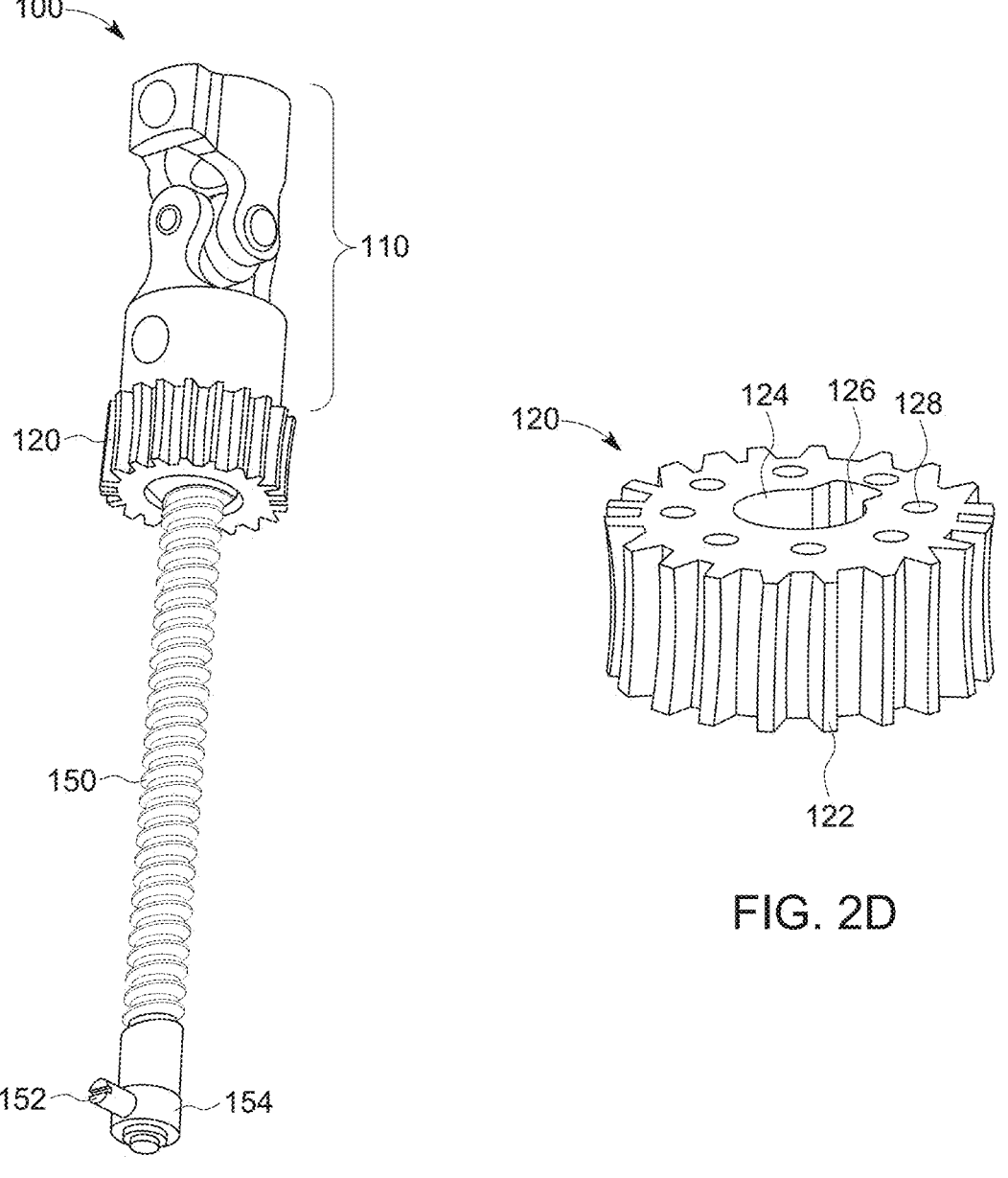

FIG. 2B illustrates strut 100 with tube 160 omitted for clarify of illustration. FIG. 2C illustrates strut 100 with tube 160, as well as quick-release mechanism 130, strut identified 140, and second joint 170 omitted for clarity of illustration.

Actuation mechanism 120 is shown isolated in FIG. 2D. Actuation mechanism 120 may be generally a short, cylindrical component with a plurality of ridges or gear teeth 122 extending around the circumference of actuation mechanism 120. The actuation mechanism 120 may be rotatably coupled to threaded rod 150 so that rotation of actuation mechanism 120 causes a corresponding rotation of threaded rod 150. For example, actuation mechanism 120 may have a channel 124 extending therethrough, with an extension 126 in channel 124 that mates with a corresponding extension in threaded rod 150, so that rotation of actuation mechanism 120 causes rotation of threaded rod 150. It should be understood that the threaded rod 150 may rotate with respect to the first joint 110, with portions of the first joint 110 and second joint 170 being rotatably fixed to rings 20 and 30, respectively. The proximal surface of actuation mechanism may include a plurality of divots or grooves 128 sized to accept a ball which is biased into the groove via a spring. The spring may have a first end in contact with a distal surface of first joint 110, with a distal end pressing a ball into the proximal surface of actuation mechanism 120. With this configuration, an amount of force is required to rotate actuation mechanism 120 to overcome the force of the spring pushing the ball into the divot 128. As rotation of actuation mechanism 120 continues, the ball will eventually be positioned adjacent to an adjacent groove 128. As rotation continues further, the spring will force the ball into the next groove 128 when the ball is aligned with the groove 128, causing a tactile and/or audible click. Each "click" may correspond to a particular axial change in length so that a user knows, for example, that four "clicks" correspond to 1 mm of length adjustment. Similar "clicking mechanisms" are described in greater detail in U.S. Pat. No. 8,834,467, the contents of which are hereby incorporated by reference herein.

Referring now to FIGS. 2A-B, quick-release mechanism 130 may generally take the form of an outer housing that surrounds a portion of threaded rod 150. Quick-release mechanism 130 may have a disengaged state and an engaged state. In the disengaged state, threaded rod 150 may be capable of moving into or out of tube 160 without rotation of the threaded rod 150, for quick adjustments of the length of strut 100, which may be useful for example while initially assembling the fixation frame 10. Rotating the quick-release mechanism 130 may transition the quick-release mechanism 130 into the engaged state, in which threaded rod 150 may only move axially into or out of tube 160 via rotation of the threaded rod 150. The mechanism for keeping the quick-release mechanism 130 in the engaged state may include a ball or other feature that is forced between adjacent threads of threaded rod 150 so that axial translation of the threaded rod 150 is only possible via rotation, so that rotation of threaded rod 150 axially moves the threaded rod 150 into the tube 160, without requiring the tube 160 to have internal threading. It should be understood that the quick-release mechanism 130 is not a necessary component of strut 100, and may be omitted from strut 100 if desired. If quick-release mechanism 130 is omitted, it may be preferably to include internal threads on tube 160 to correspond to external threads on threaded rod 150. Further details of quick-release mechanisms have been described elsewhere, including, for example, in U.S. Pat. No. 9,101,398, the contents of which are hereby incorporated by reference herein.

A strut identifier 140 may be coupled to strut 100 at any desired location, for example between the quick-release mechanism 130 and the tube 160. Strut identifier 140 may take the form of a clip or any other suitable shape that can be quickly and securely clipped onto the strut 100 and removed from strut 100. For example, in the illustrated embodiment, strut identifier 140 is a "C"-shaped clip that is flexible enough to open for easy connection to strut 100, but rigid enough that the strut identifier 140 is not easily removed from strut 100 without intentional application of force. Strut identifier 140 may have a color or other identifier such as a number, letter, or shape pattern. Each strut 100a-f may have a strut identifier 140 that is structurally similar or identical, but that each has easily distinguishable indicia, such as different colors, different numbers, etc. Strut identifiers 140 may be used so that each strut 100a-f is easily distinguished from one another, and so that other matching indicia may be provided on other components, described in greater detail below, that may be added onto struts 100a-f so that each additional component may be easily matched with the correct corresponding strut 100a-f. Strut identifier 140 may also function to prevent unintentional disengagement of the quick release mechanism 130.

Referring again to FIG. 2A, tube 160 may be a generally hollow cylindrical tube configured to allow threaded rod 150 to move axially into or out of tube 160 to decrease or increase the effective length of strut 100, respectively. As noted above, such axial movement may be produced by rotation of threaded rod 150 when the quick release mechanism 130 is in the engaged position, so that the threads of the threaded rod 150 engage the ball or other mechanism within the quick release mechanism 130. If omitting the quick release mechanism 130, the tube 160 may include internal threads that mate directly with the external threads of the threaded rod 150. A slot 162 may extend along part of the length of the tube 160, the slot 162 opening the hollow inside of the tube 160 to the exterior of the tube. The slot 162 may have a width slightly larger than the width of button 152. Referring now to FIGS. 2B-C, the distal end of threaded rod 150 may include a button 152 coupled to a collar 154, the collar 154 surrounding the distal end of threaded rod 150. Collar 154 may be positioned with a groove at the distal end of threaded rod 150 so that collar 154 may rotate freely around the axis of the strut 100 while being axially fixed with respect to the threaded of 150. Referring again to FIG. 2A, as threaded rod 150 is threaded into or out of tube 160, button 152 travels up or down the slot 162 of the tube 160, which is possible because button 152 and collar 154 are free to rotate with respect to threaded rod 150. Tube 160 may include indicia, such as hash marks and/or measurements, on or adjacent to slot 162. The position of button 152 along slot 162 may correspond to the effective length of the strut 100, so that a user can easily determine the effective length of the strut based on the indicia adjacent to the position of button 152 at any particular time.

Referring still to FIG. 2A, the distal end of tube 160 may include two extensions that form a proximal portion 171 of second joint 170. Second joint 170 may include a distal portion 175 that, together with proximal portion 171 and an internal mechanism form a universal joint similar to first joint 110. Distal portion 175 may include a first aperture 176 that is aligned substantially parallel with strut 100. Aperture 176 may be adapted to receive a fastener therein to couple second joint 170 to distal ring 30. The fastener may be a screw or other type of fastener, and may be adapted to tightly couple the second joint 170 to the distal ring 30 so that the second joint 170 does not rotate with respect to distal ring 30. With this configuration, the slot 162 of tube 160 may be positioned outward (away from the center of proximal and distal rings 20, 30) so that the position of button 152 with respect to indicia on tube 160 may be easily read at all times. The distal portion 175 of second joint 170 may include a second aperture 177 aligned substantially orthogonal to first aperture 176 and adapted to receive a tool to keep second joint 170 from rotating, for example while a fastener is screwed into first aperture 176. This may help ensure, for example, the slot 162 of tube 160 is facing away from the center of the rings 20, 30 as the strut 100 is tightened to the rings 20, 30. It should also be understood that in some prior art devices, rotational freedom of the strut was provided by loosely coupling the joint(s) to the ring(s) so that the joints themselves could swivel. In the present disclosure, the rotational degree of freedom is provided by the ability of threaded rod 150 to rotate, while the tight attachment of the first joint 110 and second joint 170 to the first ring 20 and second ring 30 provides for a more stable connection.

It should be understood that strut 100 as described above may be designed for manual actuation, for example by a user gripping the actuation mechanism 120 with his hand and manually rotating the actuation mechanism 120. However, it should be understood that a tool may be used, either directly on actuation mechanism 120 or with intervening components, to adjust the length of strut 100.

Although the struts 100a-100f shown and described in connection with FIGS. 1-2D are one type of strut suitable for use as part of an external fixation system, various other types of struts may be suitable. For example, additional types of struts are described in U.S. Patent Application Publication No. 2023/0255665 ("the '665 Publication"), the contents of which are hereby incorporated by reference herein. The '665 Publication also describes controller modules that can be used with struts to partially or fully automate strut adjustments. Still other types of struts, such as double-telescoping struts, are described in U.S. Patent Application Publication No. 2023/0193936 ("the '936 Publication"), the disclosure of which is hereby incorporated by reference herein. Various apparatus and methods are described below to assist with more precisely determining the length of a given strut at a given time during a correction procedure. Although these apparatus and methods are described in the context of particular struts, it should be understood that the apparatus and methods may be equally applicable to other types of struts, including struts 100a-100f, as well as struts disclosed in the '665 Publication and/or the '936 Publication.

When the external fixation frame is initially assembled on the patient, it is generally important to correctly identify the length of each strut. For example, in order to use software to generate a correction plan, it is generally important that the initial state of the external fixation frame, which includes the length of each strut, be correctly entered into the software. Similarly, the correction plan starts and continues, it may be important throughout the correction to confirm the length of the struts as the struts are adjusted, for example to confirm that the struts are at their correct lengths for the particular stage of the correction. If the struts are at length other than the prescribed length at the relevant stage of correction, an update to the correction plan may become required. At any of these points that the length of a particular strut needs to be known, there are up to two issues that may currently exist. First, if the lengths of the struts are manually determined (e.g., by simply viewing the struts), there is a potential source of human error that is introduced. Second, in addition to possible error, it may take an undesirable amount of time to manually determine the length of each strut (typically there are six struts in an external fixation frame), especially if the strut lengths need to be determined at multiple points from the start to the end of the correction process. Further, if strut lengths are determined using x-ray images of the external fixation frame post-implantation, errors may be introduced due to parallax errors in the x-ray images. Thus, it would be desirable to have a mechanism and/or method for accurately, quickly, objectively, and/or remotely determining the lengths of the struts of an external fixation frame at any desired point in time.

Figure 3A:
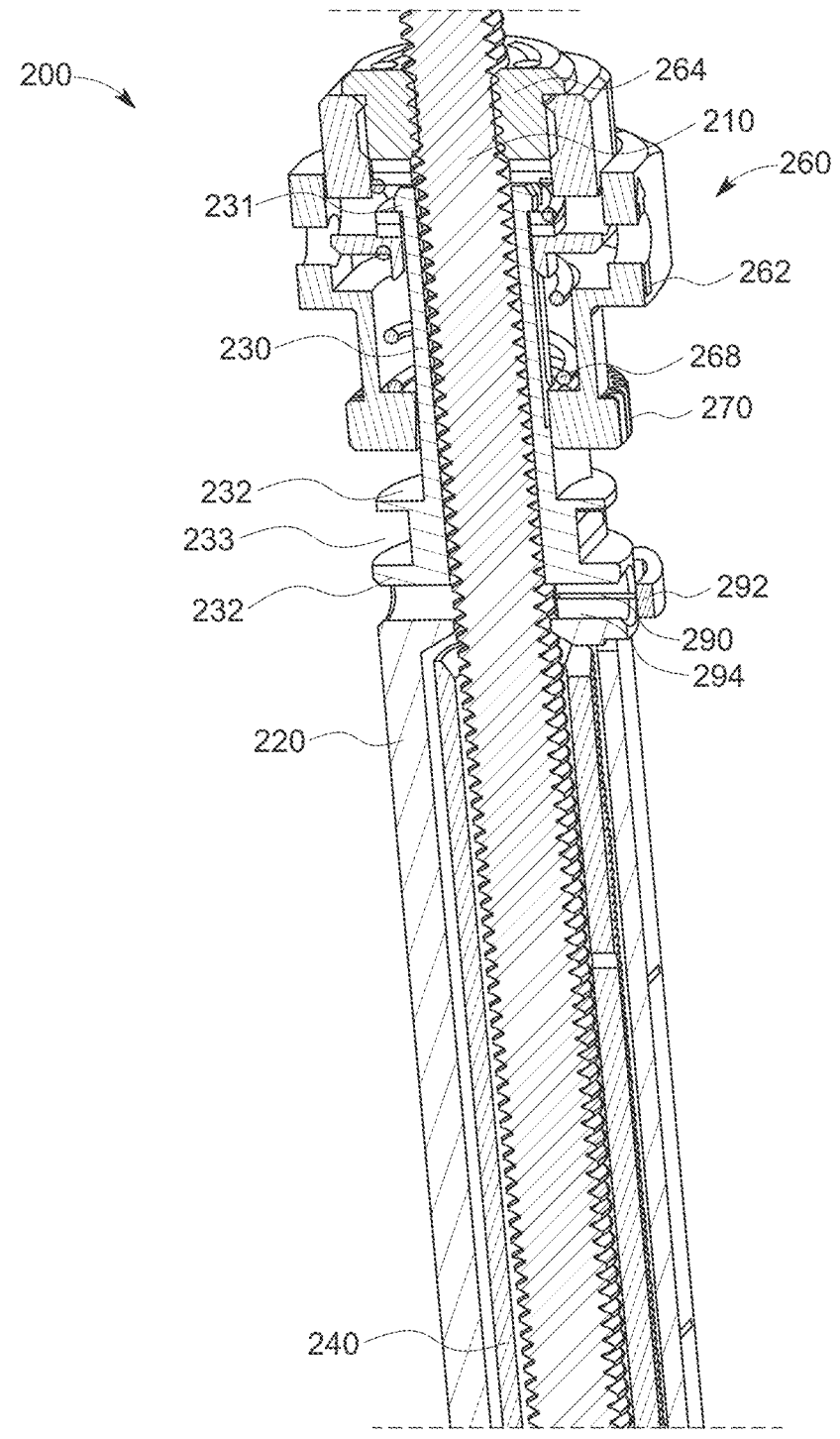
FIG. 3A is a cross-section of an example of a strut having an embodiment of a length measurement mechanism.

FIG. 3A illustrates an example of a strut 200 that has structure in common with struts described in the '936 Publication, with at least one significant difference regarding a mechanism for determining the length of the strut 200. In the illustrated embodiment, strut 200 is a double-telescoping strut that may include a threaded rod 210, one end of which may be coupled to a joint, including for example similar to joint 110. Threaded rod 210 may extend through an adjustment knob 260. In some embodiments, the adjustment knob 260 includes a correction wheel 264 that includes threading which intermeshes with threads of threaded rod 210. The adjustment knob 260 may also include a thumb knob 262. In some examples, a spring 268 or other biasing member may tend to push the thumb knob 262 away from the correction wheel 264. In the illustrated example, the thumb knob 262 is prevented from rotating until it is pulled upwardly toward the correction wheel 264, compressing the spring 268. When pulled upwardly, the thumb knob 262 is capable of rotating, which in turn rotates the thumb knob correction wheel 264 and causes the adjustment knob 260 and outer tube 220 to move axially relative to the threaded rod 210, increasing or decreasing the effective length of the strut 200. The thumb knob 262 may be connected to a gear mechanism 270 which may be manually gripped for rotation (when the spring 268 is compressed) or which may intermesh with a gear of a motorized controller (such as that described in greater detail in the '665 Publication) for partially or fully automated length adjustment of the strut 200.

Still referring to FIG. 3A, the outer tube 220 may include a plurality of flexible extensions 230 which may each end in a protrusion or lip 231 which is received within a recess in the correction wheel 264 which may, in part, keep the outer tube 220 axially fixed relative to the correction wheel 264. In the illustrated embodiment, the outer tube 220 may include one or more flanges 232 defining one or more recesses 233, which may be sized and shaped to receive a corresponding member of a motorized controller (such as that described in greater detail in the '665 Publication). In the illustrated example, the threads of the threaded rod 210 do not engage any corresponding threads within the outer tube 220. An inner tube 240 may be at least partially received within the outer tube 220, and may at least partially surround the threaded rod 210. An end of the inner tube 240 (not shown in FIG. 3A) may be coupled to a second joint, for example similar to second joint 170. In some examples, the length of the strut 200 may be gradually adjusted by rotating the adjustment knob 260 relative to the threaded rod 210. A quick adjust mechanism, not shown in FIG. 3A, may be operated to either lock the inner tube 240 relative to the outer tube 220, or to unluck the inner tube 240 relative to the outer tube 220 so that the length of the strut 200 may be rapidly adjusted, for example when initially assembling the external fixation frame 10 that uses strut 200. Examples of suitable quick adjustment mechanisms are described in greater detail in the '665 Publication.

At least one main difference between strut 200 and struts described in the '665 Publication is that strut 200 includes a mechanism for mechanically determining how much the threaded rod 210 has rotated relative to the outer tube 220, and thus how much length adjustment has occurred due to gradual adjustment of the strut 200. In the illustrated example, the length measurement mechanism may include a needle 290 or other similar structure that has a free end that is positioned to touch the external threading of the threaded rod 210. The opposite end of the needle 290 may be coupled to an arm, which may be referred to as a fluctuation counter 292. The arm or fluctuation counter 292 may have a first end coupled to (e.g., formed integrally with, or otherwise coupled mechanically or via adhesives to) outer tube 220, and extend to a free or cantilevered second end, to which the needle 290 is coupled. In the illustrated example, the outer tube 220 includes a bore 294 which allows the needle 290 to extend from the arm or fluctuation counter 292, through a wall of the outer tube 220, and into contact with the threading of the threaded rod 210.

In some examples, the fluctuation counter 292 and needle 290 are positioned so that the tip of the needle 290 tends to contact the valley of the threads of the threaded rod 210. In some examples, the "valley" of the thread may refer to the position of the thread that is closest to the central axis of the threaded rod 210. As the adjustment knob 260 is rotated to drive the threaded rod 210 axially away from the outer tube 220 (to increase the length of the strut 200) or further into the outer tube 220 (to decrease the length of the strut 200), the threads of the threaded rod 210 move axially relative to the tip of the needle 290. During this relative motion, the needle 290 is driven away from the central axis of the threaded rod 210 as the tip of the needle 290 moves from the valley of the threads toward the peaks of the threads of the threaded rod 210. In some examples, the "peak" of the thread may refer to the position of the thread that is farthest away from the central axis of the threaded rod 210. In other words, as the threaded rod 210 move axially relative to the outer tube 220 and needle 290, the needle 290 rides along the peaks and valleys of the threaded rod 210, with the tip of the needle 290 always in contact with a portion of the thread of the threaded rod 210. In some examples, the cantilevered configuration of the fluctuation counter 292 allows for some amount of flexing to allow the needle 290 to move radially inwardly toward the threaded rod 210 (when the needle 290 is moving toward a thread valley) or radially outward away from the threaded rod 210 (when the needle 290 is moving toward a thread peak). Each time the needle 290 moves through one full cycle (e.g., from one thread valley to an adjacent thread valley, or from one thread peak to an adjacent thread peak), the threaded rod 210 will have undergone exactly one complete revolution. As the needle 290 moves inwardly or outwardly, the amount of movement may be captured by the fluctuation counter 292 and each full cycle (or portion thereof) may be recorded by the fluctuation counter 292. Because the pitch of the thread of the threaded rod 210 is known, the amount of cycles of movement of the needle 290 may be directly translated into axial movement of the threaded rod 210 (and thus length change of the strut 200) by multiplying the number of cycles of movement of the needle 290 by the pitch of the thread of the threaded rod 210. The fluctuation counter 292 may be configured to detect the fluctuation in one or more ways. For example, since the needle 290 may oscillate about a mean position, at both the extremes of oscillation, switches may be mounted and/or capacitance change or resistance change can be measured to detect the fluctuations.

Figure 3B:
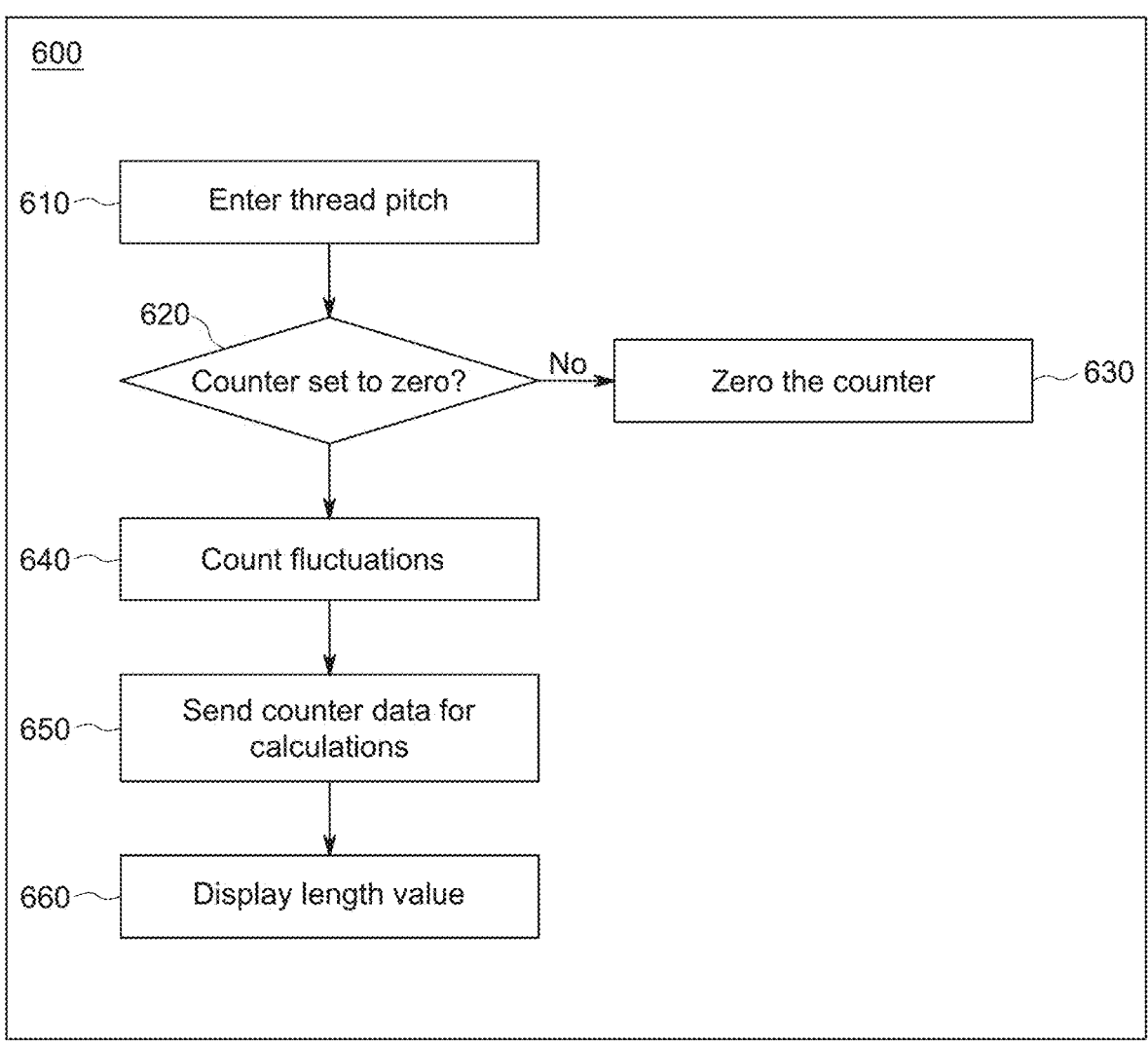
FIG. 3B is a flow chart showing example steps of a method of using the length measurement mechanism of the strut of FIG. 3A.

FIG. 3B is a flow chart of an example of a method 600 for using the length measurement mechanism of strut 200 to determine a change in length of the strut 200 during gradual length adjustment. In one example, method 600 may be performed after an external fixation frame, such as external fixation frame 10, has been implanted onto a patient using struts 200 (e.g., a total of six struts 200 in place of struts 100*a-f*). It should be understood that struts 200 may be set to an initial length using a combination of gradual and/or rapid adjustment as described above. Once the external fixation frame 10 has been implanted and is ready for use, but before correction has begun, information may be entered into fixation frame software if not already entered. For example, in step 610, a user may enter the pitch of the thread of threaded rods 210 into fixation frame software. In some examples, the fixation frame software is a web or mobile application that is used to track and/or manage the fixation frame correction. In step 620, the fluctuation counter 292 may be checked to determine if the counter is zeroed out (e.g., showing zero adjustment or showing zero length change). If the fluctuation counter 292 is not set to zero, it may be set to zero in step 630. If the fluctuation counter is set to zero, correction may proceed per the correction schedule generated by the fixation frame software. Suitable software for generating correction schedule is described in, for example, U.S. Pat. Nos. 10,194,944 and 10,154,884, the disclosures of both of which are hereby incorporated by reference herein.

As correction progresses and the lengths of the struts 200 are gradually adjusted, for example either manually or via motorized actuation of a controller coupled to the struts 200, the needle 290 rides along the threads of the threaded rod 210 between the valleys and peaks of the threads. As this occurs, the fluctuation counter 292 counts the number of total fluctuation cycles. As used herein, the term "fluctuation cycle" may refer to the movement of the needle 290 that corresponds to one full revolution of the threaded rod 210 (e.g., fluctuation from the valley of one thread to the adjacent valley, or from the peak of one thread to the adjacent peak, etc.). In some embodiments, the fluctuation counter 292 may count discrete fluctuation cycles, for example whole numbers of one, two, three, etc. fluctuations corresponding to one, two, three, etc. complete revolutions of the threaded rod 210. In other embodiments, the fluctuation counter 292 may count portions of discrete fluctuation cycles, for example including every quarter cycle, every half cycle, etc. Either way, the fluctuations of needle 290 may be counted in step 640 as the lengths of the struts 200 are adjusted to advance the correction. At any desired point in the correction, data from the fluctuation counter 292 may be transmitted to software, in step 650, that can translate the number of fluctuations counted to the total length of adjustment, for example by multiplying the total number of fluctuations (e.g., the total number of thread revolutions) by the pitch of the thread. After this calculation is performed, the length of the strut 200 (and/or the length of total adjustment of the strut 200 achieved) may be displayed in step 660 on the desired software (e.g., on a web or mobile app). In some examples, the total length of the strut 200 may be determined based on the initial starting length of the strut 200 adjusted to account for the total increase or decrease in length determined using the fluctuation counter 292. In other examples, only the total length of adjustment 200 may be provided based on the increase or decrease in length determined using the fluctuation counter 292. As should be understood, the length measurement mechanism described in connection with strut 200 and method 600 eliminates any need for ongoing manual checking of the lengths of the struts 200, which may reduce the effort needed to determine strut length as well as reduce the likelihood of errors introduced via human error.

It should be understood that, in some examples, the fluctuation counter 292 may include memory, a processor, and/or a communication module that is capable of transmitting, via a wired or wireless connection, information relating to the fluctuation count. In some examples, information regarding the thread pitch may be transmitted to the fluctuation counter 292 (e.g., after being entered into a fixation frame correction web application) so that the calculation of length adjustment can be performed within the fluctuation counter 292, and that information transmitted to an external computer such as one running a mobile or web application for planning and/or monitoring of the fixation frame progress. In some examples, if smart controller modules are being used with struts 200, for example those described in the '665 Publication, information regarding the current count of the fluctuation counter 292 may be transmitted directly to the smart controller module which may process information to determine the total length of adjustment (and/or relay information to another computer, such as one running the mobile or web application, to determine the total length adjustments). In some examples, information regarding the current count of the fluctuation counter 292 may be transmitted directly from the fluctuation counter 292 to another computer, such as one running the mobile or web application, to determine the total length adjustments.

The length measurement mechanism described in connection with strut 200 and method 600 may be highly capable of accurate reading of changes in length based on cycles of fluctuation of needle 290. However, in other examples, it may be preferably to be able to reliably read an absolute length of the strut at any given time. On such example is described below.

Figure 4A:
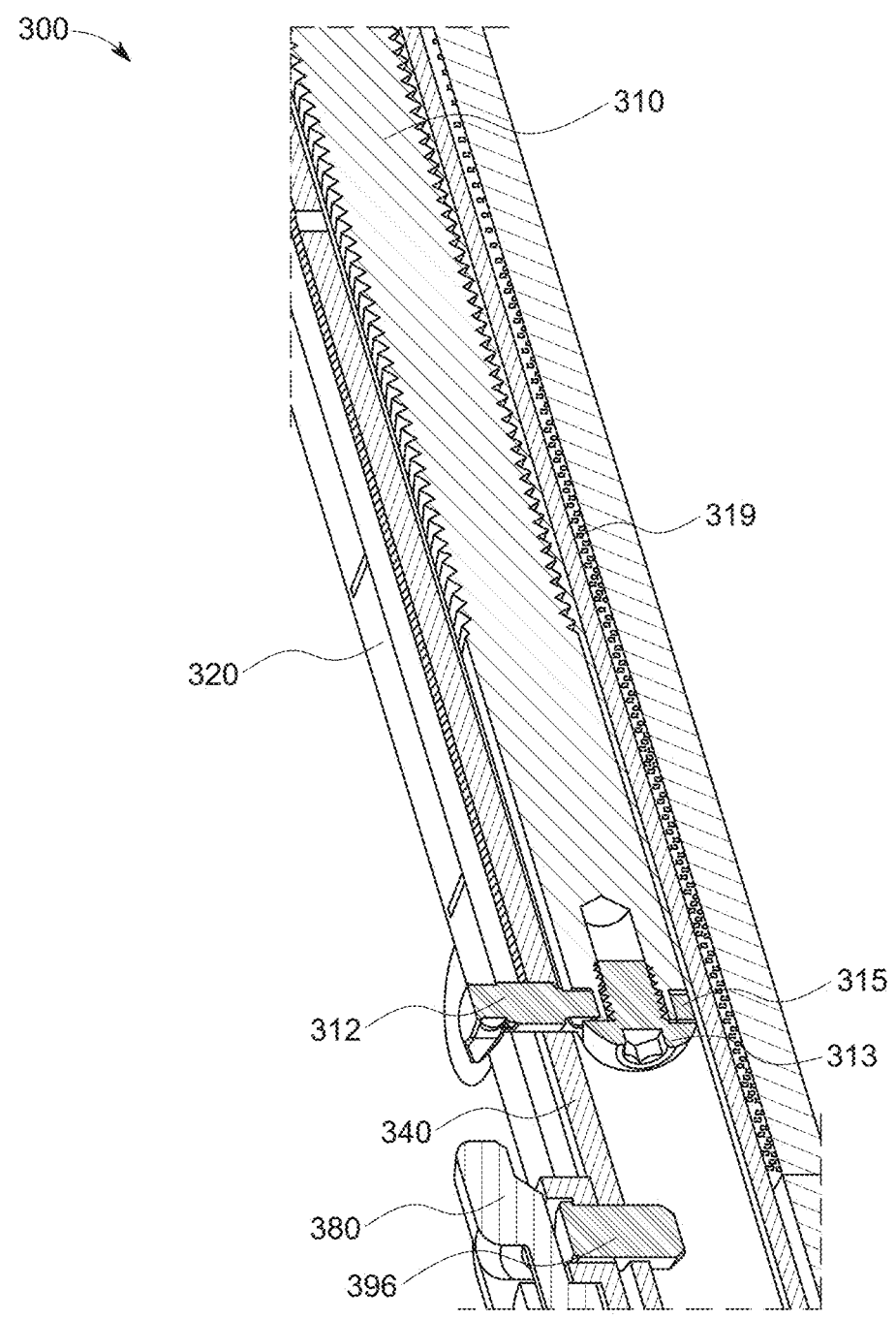
FIG. 4A is a cross-section of an example of a strut having another embodiment of a length measurement mechanism.

FIG. 4A is a cross-section of an example of a strut 300 that has structure in common with struts described in the '936 Publication, with at least one significant difference regarding a mechanism for determining the length of the strut 300. In some examples, other than the features relating to the length measurement mechanisms, strut 300 may be identical to strut 200. In the illustrated embodiment, strut 300 is a double-telescoping strut that may include a threaded rod 310, one end of which may be coupled to a joint, including for example similar to joint 110. Threaded rod 310 may extend through an adjustment knob (not shown) similar to adjustment knob 260. Threaded rod 310 may be actuated relative to the adjustment knob in the same way as described in connection with actuation of threaded rod 210 relative to adjustment knob 260, and thus these structures and functions are not described herein. It should be understood that, in the view of FIG. 4A, the adjustment knob would be on the top end of the strut 300.

Still referring to FIG. 4A, strut 300 may include an outer tube 320 that may be similar or identical to outer tube 220, with at least one exception related to the length measurement mechanism of strut 200 compared to that of strut 300. In the illustrated example, the threads of the threaded rod 310 do not engage any corresponding threads within the outer tube 320. An inner tube 340 may be at least partially received within the outer tube 320, and may at least partially surround the threaded rod 310, at least in some configurations. An end of the inner tube 340 (not shown in FIG. 4A) may be coupled to a second joint, for example similar to second joint 170. As with strut 200, in some examples, the length of the strut 300 may be gradually adjusted by rotating the adjustment knob relative to the threaded rod 310. A quick adjust mechanism 380 (which may also be referred to a gross adjustment knob, only a portion of which is shown in FIG. 4A) may be operated to either lock the inner tube 340 relative to the outer tube 320, or to unlock the inner tube 340 relative to the outer tube 320 so that the length of the strut 300 may be rapidly adjusted, for example when initially assembling the external fixation frame 10 that uses strut 300. A pin 396 may rotationally lock the inner tube 340 relative to the outer tube 320 so that the inner tube 340 and outer tube 320 can only move axially relative to each other during gross length adjustment, while staying rotationally static relative to each other. Examples of suitable quick adjustment mechanisms or gross adjustment knobs are described in greater detail in the '665 Publication.

Still referring to FIG. 4A, the terminal end of threaded rod 310, opposite the side of the top joint (e.g., similar to joint 110), may exclude threading and have a collar member to which length indicator or pointer 312 is coupled. The pointer 312 is preferably axially fixed with respect to threaded rod 310, but rotationally free. The pointer 312 may include a relatively narrow portion that is sized and shaped to protrude through axially extending slots in both the outer tube 320 and the inner tube 340. The end of pointer 312 may be wider than the width of the slots, and include extensions that are parallel to hash marks of indicia printed on the outside of the outer tube 320 and/or inner tube 340, to allow a user to manually identify what hash marks or other indicia that the pointer 312 is pointing. Collar mechanisms to allow for axial fixation but rotational freedom of pointer 312 are shown in more detail, for example, in U.S. Pat. No. 10,010,350, the disclosure of which is hereby incorporated by reference herein. As should be understood, as the threaded rod 310 rotates and telescopes into or out of the outer tube 320 (and/or into or out of the inner tube 340), the pointer 312 is capable of sliding along the slots of the inner tube 340 and outer tube 320 without rotation, even though the threaded rod 310 is rotating. Although pointer 312 is one type of length measurement mechanism, other struts described herein may include features similar to pointer 312 in case it is desired for a manual review of the current length of the strut. The length measurement mechanism of strut 300 that provides for enhanced length measurement (e.g., faster and/or more accurate measurements) is described in greater detail below.

Figure 4B:
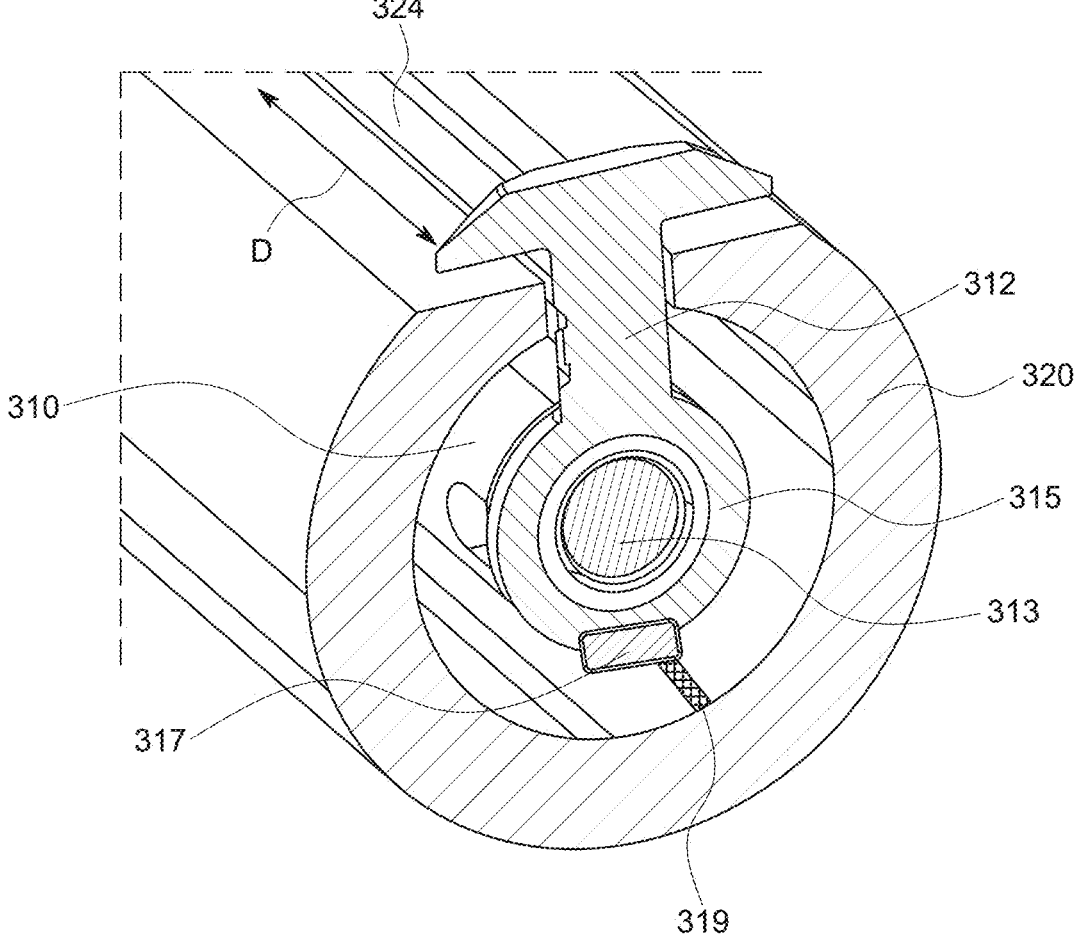
FIG. 4B is a cutaway view of a portion of the strut of FIG. 4A.

Still referring to FIG. 4A, the pointer 312 may be axially fixed to the terminal end of the threaded rod 310 via a screw 313 or other fastener which may pass through a collar 315 of the pointer 312, and into an internal bore of the threaded rod 310. It is on this collar 315 on which one component of an enhanced length measurement mechanism may be provided. FIG. 4B is a cutaway view of a portion of the strut 300 showing the terminal end of the threaded rod 310 where it connects to pointer 312 via fastener 313 extending through collar 315. It should be understood that, in the view of FIG. 4B, fastener 313 may be a screw or bolt, but the head of the screw or bolt is omitted for clarity of illustration. It should also be understood that, in the view of FIG. 4B, the strut 300 may have a configuration in which the inner tube 340 is spaced away from the threaded rod 310 so that the inner tube 340 is not visible in the FIG. 4B. In the illustrated embodiment, collar 315 is an annular or circular member that allows for the threaded rod 310 to rotate relative to the outer tube 320 while the pointer 312, via its interaction with the slot 324 of outer tube 320, restricts the pointer 312 (and collar 315) from rotating relative to the outer tube 320. Thus, as the threaded rod 310 rotates relative to the outer tube 320, the pointer 312 moves up or down through slot 324 in direction D, with the collar 315 remaining rotationally fixed relative to the outer tube 320.

At least one main difference between strut 300 and the struts described in the '665 Publication is that strut 300 includes a mechanism for automatically determining the length of the strut 300 at any particular time during the correction process. In the illustrated example of FIGS. 4A-4B, the length measurement mechanism may include a sensor 317 (which may also be referred to as an absolute linear encoder), which may be coupled to collar 315 generally opposite the extension of the pointer 312, although other positions may be suitable. The length measurement mechanism may also include a column of pits 319 formed in the inner surface of the outer tube 320 generally aligned with and confronting the position of the sensor 317. In some examples, pits 319 may be formed as laser markings, laser etchings, mechanically-formed pits, etc.

In some examples, the sensor 317 includes an array or matrix of ultrasonic sensors, or an array or matrix of optical sensors, or a camera, any of which are capable of detecting the shape of the pits 319. The pits 319 may be physical shapes that are etched into the otherwise smooth inner cylindrical surface of the outer tube 320.

Figure 4C:
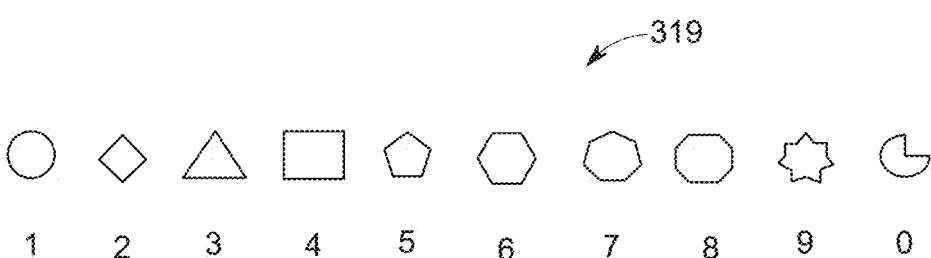
FIG. 4C is one example of a correspondence between individual codes and units of length measurement for use with the length measurement mechanism of FIGS. 4A-4B.

FIG. 4C shows an example of ten different unique shapes that may be used for pits 319. In this particular example, a circular pit 319 corresponds to the numeral one, a diamond pit 319 corresponds to the numeral two, a triangular pit 319 corresponds to the numeral three, a rectangular pit 319 corresponds to the numeral four, a pentagonal pit 319 corresponds to the numeral five, a hexagonal pit 319 corresponds to the numeral six, a septagonal pit 319 corresponds to the numeral seven, an octagonal pit 319 corresponds to the numeral eight, a seven-pointed star pit 319 corresponds to the numeral nine, and a three-quarter circle shape pit 319 corresponds to the numeral zero. It should be understood that the legend of correspondence between differently shaped pits 319 and numerals zero through nine shown in FIG. 4C are merely exemplary, and any ten unique shapes may be provided to correspond to the numerals zero through nine any desired combination.

Figure 4D:
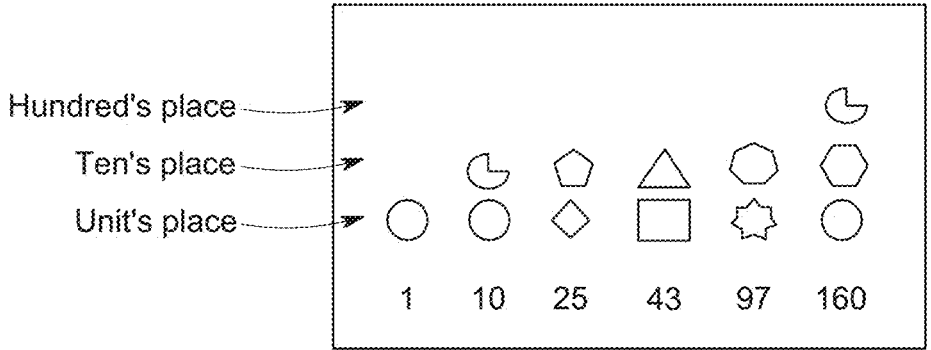
FIG. 4D shows examples of unique codes corresponding to lengths for use with the length measurement mechanism of FIGS. 4A-4B.

FIG. 4D shows examples of unique codes of pits 319 corresponding to specific lengths. In some examples, the column of pits 319 may be provided as three adjacent columns, with one column representing the single unit place, the next column representing the tens place, and the following column representing the hundreds place. FIG. 4D shows an example of various rows of pits 319 that may be positioned at different places along the length of the column of pits 319. For example, a row of pits 319 that includes only a circular pit 319 in the single unit place may correspond to the numeral one. A row of pits 319 that includes a circular pit 319 in the single unit place and a three-quarter circle shape pit 319 in the tens place may correspond to the numeral ten (the numeral one followed by the numeral zero). A row of pits 319 that includes a rectangular pit 319 in the single unit place and a triangular pit 319 in the tens place may correspond to the numeral forty-three (the numeral four followed by the numeral three). As one final example, a row of pits 319 that includes a circular pit 319 in the single unit place, a hexagonal pit 319 in the tens place, and a three-quarter circle shape pit 319 in the hundreds place may correspond to the numeral one hundred sixty (the numeral one followed by the numeral six followed by the numeral zero). It should be understood that the options shown in FIG. 4D are merely exemplary individual options, based on the legend of FIG. 4C, to show how rows of pits corresponding to up to one-thousand unique numbers may be formed in the inner surface of the outer tube 320 if using three rows of pits 319.

In one example, the pits 319 may be formed in the inner surface of the outer tube 320 so that each row represents a number that corresponds to the length of the strut 300 when the sensor 317 is aligned with the particular row of pits 319. In other words, the pits 319 may be formed so that the unique combination of shapes of pits 319 provides sequential numbering that is representative of length. For example, when the sensor 317 is aligned with a row of pits 319 that have shapes corresponding to the numeral one hundred, at that position of the threaded rod 310 relative to the outer tube 320, the length of the strut 300 may be one hundred millimeters. Again, it should be understood that the specific numbers and shapes of pits 319 described herein are merely exemplary of the concept.

Figure 4E:
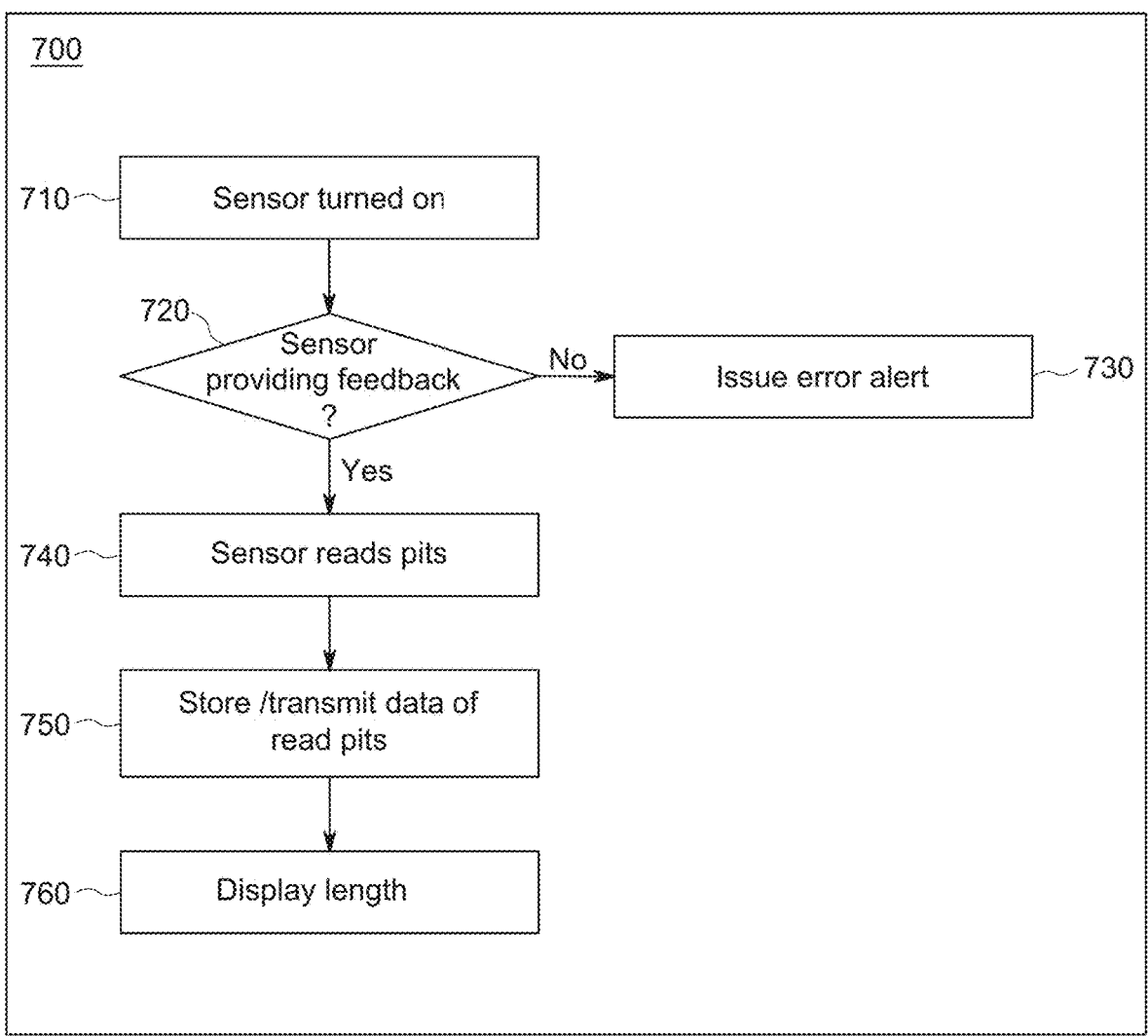
FIG. 4E is a flow chart showing example steps of a method of using the length measurement mechanism of the strut of FIGS. 4A-4B.

FIG. 4E is a flow chart of an example of a method 700 for using the automated length measurement mechanism of strut 300 to determine an absolute length of the strut 300 at any point during the correction procedure. In one example, method 700 may be performed after an external fixation frame, such as external fixation frame 10, has been implanted onto a patient using struts 300 (e.g., a total of six struts 300 in place of struts 100a-f). In a first example step 710, the sensor 317 (which may also be referred to as an absolute linear encoder) is turned on, and in step 720 it is determined whether the sensor 720 is providing any feedback. If it is determined that no feedback is being provided, in example step 730, an error alert may be issued to the user in order to allow for troubleshooting. If it is determined that feedback is being provided, in example step 740, the sensor 317 may read the particular row of pits 319 on the inner surface of the outer tube 320 that the sensor 317 confronts. This data may be stored within memory on (or operably coupled to) the sensor 317 for immediate or future transmission to a computer system that may, in step 760, display the length of the strut 300 based on the unique combination of pits 319 read by the sensor 317. It should be understood that, because the sensor 317 is positioned on the collar 315 of the pointer 312, and because the pits 319 are provided in a column on the inner surface of the outer tube 320 in alignment with the sensors 317, the sensor 317 will always face the pits 319 due to the point 312 (and collar 315 and sensor 317) being rotationally fixed to the outer tube 320 (and pits 319).

It should be understood that, in some examples, the sensor 317 may include memory, a processor, and/or a communication module that is capable of transmitting, via a wired or wireless connection, information relating to information determined from reading pits 319. In some examples, information regarding the unique codes of pits 319 may be transmitted to the sensor 317 so that the calculation of total length correlating to the unique code of pits 319 can be performed within the fluctuation sensor 317, and that information transmitted to an external computer such as one running a mobile or web application for planning and/or monitoring of the fixation frame progress. In some examples, if smart controller modules are being used with struts 300, for example those described in the '665 Publication, information regarding the data of pits 319 read by the sensor 317 may be transmitted directly to the smart controller module which may process information to determine the total length the strut 300 (and/or relay information to another computer, such as one running the mobile or web application, to determine the total length adjustments). In some examples, information regarding the data of pits 319 read by the sensor 317 may be transmitted directly from the sensor 317 to another computer, such as one running the mobile or web application, to determine the total length adjustments.

One of the benefits of the automated length measurement described in connection with strut 300 is that a unique signal can be provided by pits 319 for any given length of the strut 300. Because of this, a zero-point reference is not required for using this type of length measurement, for example because it is not changes that are being measured or determined, but rather absolute values that are being read directly by the sensor 317 at any given length of the strut 300. Even if the sensor 317 or related component has been turned off of lost power for a certain amount of time, re-calibration is not needed.

Figure 5A:
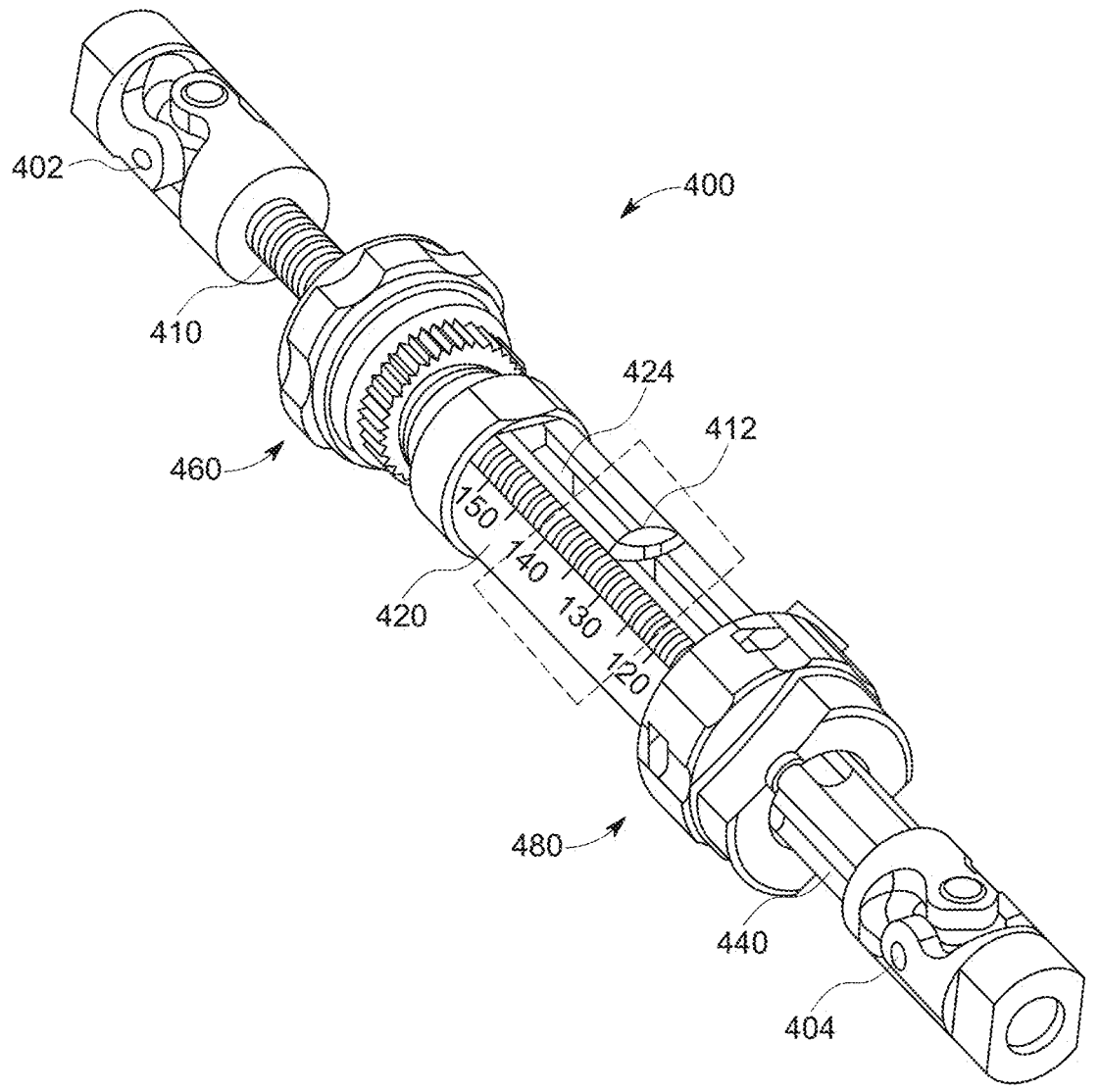
FIG. 5A is a perspective view of an example of a strut having another embodiment of a length measurement mechanism.

FIG. 5A is a perspective view of an example of a strut 400 that has structure in common with struts described in the '936 Publication, with at least one significant difference regarding a mechanism for determining the length of the strut 400. In some examples, other than the features relating to the length measurement mechanisms, strut 400 may be identical to struts 200 and 300. In the illustrated embodiment, strut 400 is a double-telescoping strut that may include a threaded rod 410, one end of which may be coupled to a joint 402. Threaded rod 410 may extend through adjustment knob 460, which may be similar or identical to adjustment knob 260. Threaded rod 410 may be actuated relative to the adjustment knob 460 in the same way as described in connection with actuation of threaded rod 210 relative to adjustment knob 260.

Still referring to FIG. 5A, strut 400 may include an outer tube 420 that may be similar or identical to outer tube 220, with at least one exception related to the length measurement mechanism of strut 200 compared to that of strut 400. In the illustrated example, the threads of the threaded rod 410 do not engage any corresponding threads within the outer tube 420. An inner tube 440 may be at least partially received within the outer tube 420, and may at least partially surround the threaded rod 410, at least in some configurations. An end of the inner tube 440 may be coupled to a second joint 404, for example similar to second joint 170. As with struts 200 and 300, in some examples, the length of the strut 400 may be gradually adjusted by rotating the adjustment knob 460 relative to the threaded rod 410. A quick adjust mechanism 480 may be operated to either lock the inner tube 440 relative to the outer tube 420, or to unluck the inner tube 440 relative to the outer tube 420 so that the length of the strut 400 may be rapidly adjusted, for example when initially assembling the external fixation frame 10 that uses strut 400.

Still referring to FIG. 5A, the terminal end of threaded rod 410, opposite the side of the top joint 402, may exclude threading and have a collar member to which length indicator or pointer 412 is coupled. The pointer 412 may be similar or identical to pointer 312, and is thus not described again here, except that the sensor 319 on pointer 312 may be omitted from pointer 412. As with strut 300, as the threaded rod 410 moves into or out of the outer tube 420 as the length of the strut 400 increases or decreases, the pointer 412 may move axially along slot 424. In some examples, optical marking may be provided on the outer tube 420 that the pointer 412 may align with. Although in FIG. 5A the markings on the outer tube 420 are shown as hash marks with length indicators, it should be understood that the markings may instead be optical markers.

Figure 5B:
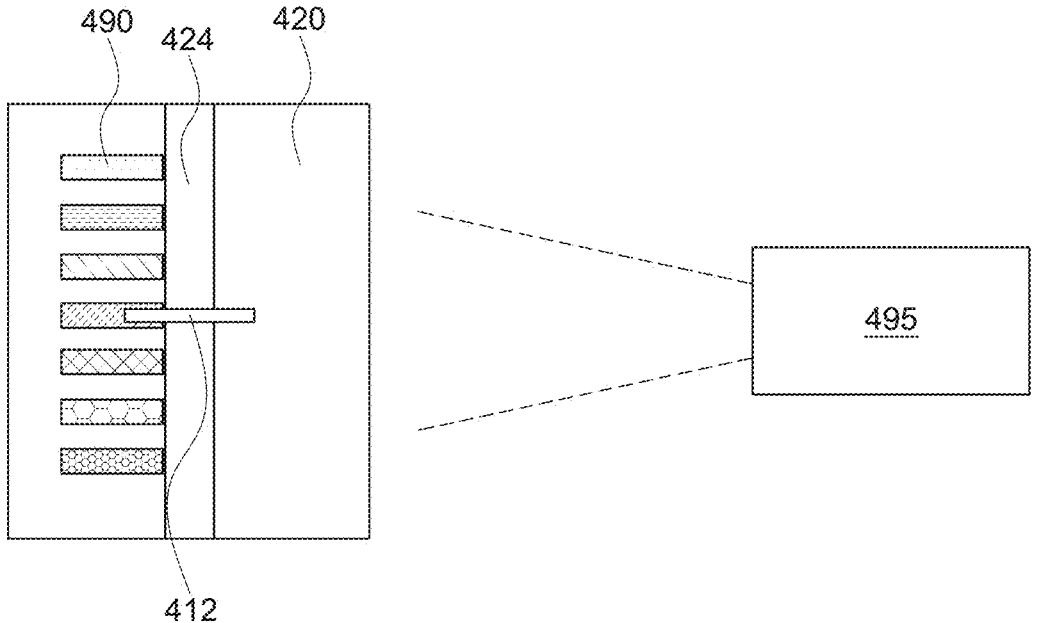
FIG. 5B is an enlarged view of an example of a portion of the strut of FIG. 5A within the dashed box of FIG. 5A.

FIG. 5B is an enlarged view of the portion of strut 400 in FIG. 5A bounded in a dashed rectangle. In the view of FIG. 5B, the pointer 412 is shown extending through the slot 424 of tube 420. A plurality of optical markings 490 are provided on the outer tube 420 adjacent the slot 424. Each optical marking 490 may be any suitable unique marking that is readable by a camera 495 or other scanner. Each unique marking 490 may correspond to a length of the strut 400 when the pointer 412 is aligned with a particular marking 490. In use, a camera 495 may be pointed at any strut 400. In some examples, camera 495 may be a smart phone camera of a user, but in other examples the camera 495 may be any suitable standalone camera or otherwise a camera coupled a component of the fixation frame 10. In use, when the camera 495 is pointed at a particular strut 400 similar to the configuration of FIG. 5B, the camera 495 (or software running on a computer, such as a smart phone operatively coupled to the camera 495) may determine which optical marking 490 is overlapped by the pointer 412, and determine that the optical marking 490 overlapped by the pointer 412 is the relevant optical marking 490 to read. In some examples, the optical markings 490 may be read by a camera 495 in a similar fashion as optical mark recognition ("OMR") and/or optical character recognition ("OCR"). Upon determining which optical marking 490 is overlapped by the pointer 412, the camera 495 may read that particular optical marking 490 and translate the pattern or characters on the optical marking 490 to the corresponding unique length of strut 400. In some examples, if the camera 495 is part of a smart phone, an application being used to operate the camera 495 may overlay the actual length measurement information onto the image of the strut 400 shown on the smart phone screen. With this embodiment, the absolute length of the strut 400 may be determined by the camera 495 recognizing the relevant optical marking 490 that the pointer 412 aligns with, and provide a quick and accurate measurement reading to the user.

FIG. 6A is front view of an example of a strut 500, shown in partial phantom, having another embodiment of a length measurement mechanism. Strut 500 is shown in generally simplified form, but may have the same overall components as struts 200, 300, 400, with the exception of the particular mechanism for automatically measuring the overall length of the strut 500. As such, these components or not described in greater detail herein, other than to state that the strut 500 may include an inner tube 540 coupled to a joint 504, the inner tube 540 being positioned within an outer tube 520. The outer tube 520 may house a threaded rod (not separately labeled) similar to threaded rods 210, 310, 410, with the threaded rod being coupled to another joint 502.

As with other double-telescoping struts described herein, the total length of the strut 500 may be based on two length components. A first length component may be an acute or rapid length adjustment achieved by moving the inner tube 540 farther out of or farther into the outer tube 520, for example using a locking mechanism such as any of the quick adjust mechanisms (or gross adjustment knobs) described above. As with other embodiments described herein, this acute or rapid adjustment may be performed when initially assembling the external fixation frame 10 to the patient, which includes assembling the struts 500 to the rings 20, 30. A second length component may be a gradual length achievement achieved by moving the threaded rod farther out of or farther into the outer tube 520, for example using a gradual adjustment knob which may be similar to adjustment knobs 260, 460 described above.

In the illustrated example of FIG. 6A, a first resistance wire 590 may be provided in the outer tube 520 with both ends connected to a connector 594. A second resistance wire 591 may be provided in the inner tube 540 having points of contact with the first resistance wire 590. A third resistance wire 592 may be provided on the threaded rod, the third resistance wire 592 having a point of contact 593 with the first resistance wire 590, the third resistance wire 592 also being coupled to the connector 594. In use, the three resistance wires 590, 591, 592 may create two separate loops from the connector 594 through the three moving components of the strut 500, such that as the overall strut 500 length changes due to acute length adjustment, a first effective length L1 of the resistance wire changes in one area of one of the loops, and while overall strut 500 length changes due to gradual length adjustment, a second effective length L2 of the resistance wire changes in a second area of the other loop. As will be explained in greater detail below, one of the effective loop lengths changes only during gradual correction, while the other effective loop length changes only during rapid or acute length change.

This electrically conductive wire loop is shown in isolation schematically in FIG. 6B. In the schematic illustration of FIG. 6B, the third resistance wire 592 extends from a connection point 594b of the connector 594 to a point of contact 593. As noted above the third resistance wire 592 moves up or down with movement of the threaded rod, changing the position of the point of contact 593 that connects the third resistance wire 592 to the first resistance wire 590, and specifically a first portion 590a of the first resistance wire 590. The first portion 590a of the first resistance wire 590 may have a first end 590c that connects back to connector 594 at connection point 594a, creating a first electronically conductive loop. The first portion 590a of the first resistance wire 590 may have another end that terminates in a point of connection 590a1 that contacts one leg of the second resistance wire 591. Similarly, a second portion 590b of the first resistance wire 590 may terminate in a point of connection 590b1 that contacts the other leg of the second resistance wire 591, with the second portion 590b of the first resistance wire 590 also connecting to connector 594 but at connection point 594c.

During gradual correction, the point of contact 593 between the third resistance wire 592 and the first portion 590a of the of the first resistance wire 590 changes (for example as the threaded rod, not shown, advances into or out of the outer tube 520). Thus, during gradual correction, the overall length of a first wire loop changes, the first wire loop extending from connection 594b of connector 594, along third resistance wire 592, down the first portion 590a of the first resistance wire 590, along second resistance wire 591, and back up the second portion 590b of the first resistance wire 590 back to connector 594 at connection point 594c.

Thus, if an external device is connected to connections 594*b* and 594*c*, and power is applied to connector 594 at connection 594*b*, electricity moves through the first loop of resistance wires back to the connector 594. As one particular example, current may flow through the third resistance wire 592, down the first portion 590*a* of the first resistance wire 590, along second resistance wire 591, and back to connector 594 via the second portion 590*b* of the first resistance wire 590. A resistance determined based on the electricity flowing through this first loop may represent the total current length of the strut, based on the sum of the acute length and the gradual length. However, before being able to determine the total length of the strut, the acute length of the strut may be determined.

During acute adjustment, as the inner tube 540 moves during acute or gross strut length adjustment, the points of connection 590*a*1, 590*b*1 change where they make contact with the respective legs of the second resistance wire 591. Thus, if an external device is connected to connections 594*a* and 594*c*, and power is applied to connection 594*a* of connector 594, in one example, electricity moves through a second loop of resistance wires back to the connector 594. As one particular example, in this second loop, current may flow along the third portion 590*c* and then the first portion 590*a* of the first resistance wire 590, into the second resistance wire 591 via connection point 590*a*1, then into second portion 590*b* of the first resistance wire 590 via connection point 590*b*1, and then back to the connector 594 via third connection 594*c*. This second loop may result in a resistance equal to the resistance of the gradual length (a constant, known value) and the effective resistance of the acute length. Thus, the resistance resulting from interrogating this second loop may allow for the acute length of the strut to be determined (using the known constant of the maximum gradual length). Then, the resistance resulting from interrogating the first loop may provide a resistance value that corresponds to the total strut length, and since the total strut length is equal to the sum of the gradual and acute strut lengths, and the acute strut length was calculated via the interrogation of the second loop, the interrogation of the first loop may allow for the gradual strut length to be calculated. In other words, via these two example interrogations of two different loops, the resulting resistances can be used to determine both the acute strut length and the gradual strut length.

By Ohm's law, in which voltage is equal to the product of current and resistance, as current is applied to each individual circuit (the first wire loop and the second wire loop), the total length of each circuit may be determined by applying current and measuring voltage. The determined resistance may be calibrated to determine actual strut length, as described below. In some examples, as shown in FIG. 6C, a portable device 800, which may have its own power source, may include a connector 894 configured to couple to connector 594 of strut 500. Power (e.g., 3.3 volts) may be applied from the portable device 800 to each individual circuit, with the resistance of each circuit being determined by applying Ohm's law where the voltage and current is known. Based on a prior calibration step (described in more detail below), the calculated resistance may be used to determine the total length of strut 500, which may be displayed on a screen of the portable device 800. In some examples, a 16-bit ADC (analog-to-digital) converter may be used with portable device 800 to measure the circuit voltage and convert it to digital form. With the resolution of a 16-bit ADC, and using a 100 mm resistance wire that corresponds to the maximum strut length, the accuracy of the system may be high enough to detect length changes with a resolution of 0.001 mm.

In some examples, the system (including struts 500 and portable device 800) may be calibrated during the manufacturing process, although the option remains to calibrate the system at another later point by using the calibration device. In one example, during calibration, the strut 500 may be adjusted to its minimum possible length, as shown in FIG. 6D, and a calibration device 850 may be connected to portable device 800. As a second part of the calibration, the strut 500 may be adjusted to its maximum possible length, as shown in FIG. 6E, and the calibration device 850 may be connected to portable device 800. In both stages of calibration, the resistance determined by portable device 800 may be calibrated to the strut length which is entered into the calibration device 850 during the calibration steps. Based on this calibration, the portable device 800 will be able to determine the total length of the strut 500 based on resistance values at any length between the minimum and maximum lengths of the strut 500.

In some examples, features may be provided to assist with auto-detection of the type of strut (e.g., long strut, medium strut, short strut, extra short strut, mini strut) as well as the location of the strut (e.g., position one through six if six struts are used). In such examples, two components may be leveraged to detect the type and position of the strut. For example, each type of strut 500 may be provided with a unique internal resistance. For example, FIG. 6F shows a medium size strut 500 which may include an internal resistance $\Omega 1$ of 8 Ohms. Other size struts may be provided with different internal resistances, such as a long strut having an internal resistance of 10 Ohms, a short strut having an internal resistance of 6 Ohms, an extra short strut having an internal resistance of 4 Ohms, and a mini strut having an internal resistance of 2 Ohms. A second component to leverage the strut position may be a strut clip 900, shown in FIGS. 6G-6H. The strut clip 900 may have a color and/or number unique to each strut. The strut clip 900 shown in FIGS. 6G-6H is meant to identify the second strut and be coupled to the second strut, as shown in FIG. 6I. The strut clip 900 may be provided with its own internal resistance $\Omega 2$. If six struts 500 are used, a total of six strut clips 900 may be used, each strut clip 900 having a different internal resistance $\Omega 2$. For example, the strut clip 900 for the first strut position may have an internal resistance of 10 Ohms, the strut clip 900 for the second strut position may have an internal resistance of 20 Ohms, the strut clip 900 for the third strut position may have an internal resistance of 30 Ohms, the strut clip 900 for the fourth strut position may have an internal resistance of 40 Ohms, the strut clip 900 for the fifth strut position may have an internal resistance of 50 Ohms, and the strut clip 900 for the sixth strut position may have an internal resistance of 60 Ohms.

When a strut clip 900 is attached to its corresponding strut 500, the internal resistance $\Omega 1$ of the strut (based on type of strut) and the internal resistance $\Omega 2$ of the strut clip 900 (based on position of strut) are combined, resulting in a unique resistance value. This value may be measured by the ADC in the portable device 800 to identify the specific location and strut type. For example, referring to FIG. 6I, when the strut clip 900 of the second position (having an internal resistance $\Omega 2$ of 20 Ohms) is connected to a medium-length strut 500 (having an internal resistance $\Omega 1$ of 8 Ohms), the total resistance of the system is 28 Ohms, providing a unique resistance value that allows for identification of both the type of strut (e.g., length-type of strut) and the position of the strut (e.g., positions one through six).

Based on the example values of internal resistances $\Omega 1$ of the different type of struts and internal resistances $\Omega 2$ of the different type of position strut clips 900, a chart is provided in FIG. 6J showing how all combinations of strut types and strut positions provide for a unique total resistance value that can identify uniquely the position and type of each strut 500.

In use, when it is desired to measure the length of one or more of the struts 500, the portable device 800 (after calibration has previously performed) may be coupled to a corresponding strut 500 by connecting connector 894 to connector 594. By determining the combined internal resistance of the strut 500 and the clip 900 (e.g., $\Omega 1+\Omega 2$), the portable device 800 may determine which position strut it is connected to, as well as what type of strut it is connected to. As described above, the portable device 800 may apply power to the strut 500 and, based on the resistances of the resistance wire loops, the length of the strut 500 may be determined. In some examples, the length of the strut 500 may be stored along with identifying information about the type and position of the strut 500. In some examples, each strut 500 may be measured individually, and after each measurement, the portable device 800 may transmit, e.g. via Bluetooth or any other suitable communication modality, the length and identification of the strut, for example to web or mobile software that manages the correction schedule. In some examples, each strut 500 may be measured by the portable device 800, and then all strut length measurements (along with corresponding strut identification information) may be transmitted together to the web or mobile application managing the correction schedule. In some examples, instead of transmitting the information wirelessly, the strut lengths and identification may be displayed on the portable device 800 for the user to enter manually into the relevant software application as desired.

FIGS. 6K-L illustrate other examples of interrogating resistance wires in struts to calculate the relevant lengths of those struts, generally similar to those shown in FIGS. 6A-B. It should be understood that the disclosure provided in connection with FIGS. 6C-6J may similarly apply to the example of FIGS. 6K-L.

FIG. 6K is front view of an example of a strut 1500, with center portions thereof shown in partial phantom, having another embodiment of a length measurement mechanism, similar to that of FIG. 6A. Strut 1500 may have the same overall components as struts 200, 300, 400, with the exception of the particular mechanism for automatically measuring the overall length of the strut 1500. As such, these components or not described in greater detail herein, other than to state that the strut 1500 may include an inner tube 1540 coupled to a joint 1504, the inner tube 1540 being positioned within an outer tube 1520. The outer tube 1520 may house a threaded rod 1510 similar to threaded rods 210, 310, 410, with the threaded rod being coupled to another joint 1502.

As with other double-telescoping struts described herein, the total length of the strut 1500 may be based on two length components. A first length component may be an acute or rapid length adjustment achieved by moving the inner tube 1540 farther out of or farther into the outer tube 1520, for example using a locking mechanism, such as quick adjustment mechanism 1580, which may be similar or identical to any of the quick adjust mechanisms (or gross adjustment knobs) described above. As with other embodiments described herein, this acute or rapid adjustment may be performed when initially assembling the external fixation frame 10 to the patient, which includes assembling the struts 1500 to the rings 20, 30. A second length component may be a gradual length achievement achieved by moving the threaded rod 1510 farther out of or farther into the outer tube 1520, for example using a gradual adjustment knob 1560, which may be similar to adjustment knobs 260, 460 described above.

Now referring to both FIGS. 6K and 6L, a first resistance wire 1590 may include a first end connected to connector 1594, for example at connection 1594*b*. A fourth portion 1590*d*1 of first resistance wire 1590 may extend from the connection 1594*b* and include a first portion 1590*a*1 extending downward from an end of fourth portion 1590*d*1 toward inner tube 1540, and a third portion 1590*c*1 extending upward from an end of fourth portion 1590*d*1 toward threaded rod 1510, where it may loop backward toward connector 1594. A third resistance wire 1592 may include a first end coupled to connection 1594*a* of connector 1594, and terminate in a second end with a contact point 1593 that can ride along the looped back portion of the third portion 1590*c*1 of first resistance wire 1590 as the threaded rod 1510 moves farther into or out of the outer tube 1520. A second resistance wire 1591 may be positioned on or in inner tube 1540 similar to second resistance wire 591. For example, the first portion 1590*a*1 of first resistance wire 1590 may terminate in a contact point with a first leg of the third resistance wire 1591, and a second portion 1590*b*1 of the first resistance wire 1590 may have a first end that terminates in a contact point with a second leg of the third resistance wire 1591, and a second end that connects to a connection 1594*c* of connector 1594. It should be understood that, although the term "connection wire" is used herein, the term "connection wire" does not necessarily refer to a single continuous wire, but rather may include multiple wire portions.

Referring mainly to FIG. 6L, this configuration may generally create two loops, with a first loop generally corresponding to the gradual length (e.g., L2 of FIG. 6K) and a second loop generally corresponding to the acute length (e.g., L1 of FIG. 6K). For example, in order to measure the gradual length, a portable device 800 may be connected to connections 1594*a* and 1594*b* of connector 1594, and power applied to one of the connections. With this configuration, electric current may flow along third resistance wire 1593, then to the third portion 1590*c*1 of the first resistance wire 1590 and then to the fourth portion 1590*d*1 of the first resistance wire 1590, back to the connector 1594 at connection point 1594*b*. As the threaded rod 1510 moves farther into or out of the outer tube 1520, the effective length of the first loop changes, resulting in a corresponding change in effective resistance of the loop. In order to measure the acute length, a portable device 800 may be connected to connections 1594*b* and 1594*c* of connector 1594, and power applied to one of the connections. With this configuration, electric current may flow along the fourth portion 1590*d*1 of the first resistance wire 1590, down the first portion 1590*a*1 of the first resistance wire, along the second resistance wire 1591, and back up the second portion 1590*b*1 of the first resistance wire 1590 back to the connector 1594 at connection 1594*c*. As the inner tube 1540 moves farther into or out of the outer tube 1520, the effective length of the second loop changes, resulting in a corresponding change in effective resistance of the loop. Thus, the gradual and acute length may each be detected directly by determining the resistance of each loop individually and comparing to the known reference values, and the total length of the strut may be determined by summing the acute and gradual lengths.

Although the invention herein has been described with reference to particular embodiments, it is to be understood that these embodiments are merely illustrative of the principles and applications of the present invention. For example, features described in relation to one particular embodiment may be combined with features of other embodiments described herein. It is therefore to be understood that numerous modifications may be made to the illustrative embodiments and that other arrangements may be devised without departing from the spirit and scope of the present invention as defined by the appended claims.

The invention claimed is:

1. A strut for use with an external fixation system, the strut comprising:

a first joint proximate a first end of the strut, the first joint configured to couple to a first ring of the external fixation system;

a second joint proximate a second end of the strut, the second joint configured to couple to a second ring of the external fixation system;

a threaded rod having a first end coupled to the first joint;

a tube that receives the threaded rod;

a fluctuation counter coupled to the tube; and a needle coupled to the fluctuation counter, the needle extending through a bore in the tube, the needle having a free end in contact with the threaded rod, wherein the strut is an adjustable-length strut whereby the threaded rod is moveable axially into or out of the tube, and while the threaded rod moves into or out of the tube, the free end of the needle is configured to maintain contact with the threaded rod.

2. The strut of claim 1, wherein while the threaded rod moves into or out of the tube, the free end of the needle is configured to maintain contact with the threaded rod by riding along peaks and valleys of threads of the threaded rod.

3. The strut of claim 2, wherein as the free end of the needle rides along peaks and valley of threads of the threaded rod, a position of the fluctuation counter is configured to fluctuate relative to the tube.

4. The strut of claim 3, wherein the fluctuation counter is configured to count a total number of fluctuations as the free end of the needle rides along peaks and valleys of threads of the threaded rod, with one fluctuation corresponding to one complete revolution of the threaded rod.

5. A method of determining a change in length of a strut of an external fixation system, the method comprising:

axially translating a threaded rod of the strut into or out of a tube of the strut to increase or decrease an effective length of the strut such that, during the axial translating, a free end of a needle that is coupled to a fluctuation counter that is coupled to the tube moves radially inward toward thread valleys of the threaded rod or radially outward toward threads peaks of the threaded rod;

counting, via the fluctuation counter, a total number of fluctuation cycles of the needle, each fluctuation cycle corresponding to one revolution of the threaded rod relative to the tube; and determining a total length change of the strut by multiplying the total number of fluctuation cycles by a pitch of the threaded rod.

6. The method of claim 5, wherein each time the free end of the needle moves from one peak of the threaded rod to an axially adjacent peak of the threaded rod, the fluctuation counter increases the total number of counted fluctuation cycles by one.

7. The method of claim 6, wherein prior to determining the length change of the strut, the pitch of the threaded rod is entered into software of a computer system.

8. The method of claim 7, wherein after counting the total number of fluctuation cycles of the needle, the total number of counted fluctuation cycles is entered into the software of the computer system, and the step of determining the total length change of the strut is performed using the software of the computer system.

9. The method of claim 5, wherein each time the free end of the needle moves from one valley of the threaded rod to an axially adjacent valley of the threaded rod, the fluctuation counter increases the total number of counted fluctuation cycles by one.

10. The method of claim 5, wherein prior to counting the total number of fluctuation cycles of the needle, the total number of counted fluctuation cycles is set to zero.

* * * * *